（12) United States Patent
Rothstein et al.

US008586825B2

(10) Patent No.: US 8,586,825 B2
(45) Date of Patent: *Nov. 19, 2013

(54) NITROGEN-REGULATED SUGAR SENSING GENE AND PROTEIN AND MODULATION THEREOF

(75) Inventors: Steven Rothstein, Guelph (CA); Yong-Mei Bi, Guelph (CA)

(73) Assignee: The University of Guelph, Ontario (CA)

( * ) Notice: Subject to any disclaimer, the term of this patent is extended or adjusted under 35 U.S.C. 154(b) by 934 days.

This patent is subject to a terminal disclaimer.

(21) Appl. No.: 12/494,171

(22) Filed: Jun. 29, 2009

(65) Prior Publication Data

US 2009/0276919 A1 Nov. 5, 2009

Related U.S. Application Data

(62) Division of application No. 11/331,199, filed on Jan. 13, 2006, now Pat. No. 7,554,018.

(60) Provisional application No. 60/643,575, filed on Jan. 14, 2005.

(51) Int. Cl.
*C12N 15/09* (2006.01)
*C12N 15/82* (2006.01)
*A01H 5/00* (2006.01)

(52) U.S. Cl.
USPC ........... 800/278; 800/287; 800/284; 800/290; 800/317.3; 800/320.2; 800/320.1; 800/298

(58) Field of Classification Search
None
See application file for complete search history.

(56) References Cited

U.S. PATENT DOCUMENTS

| 7,196,245 | B2 | 3/2007 | Jiang et al. | |
| 7,554,018 | B2 * | 6/2009 | Rothstein et al. | 800/320 |
| 2004/0123343 | A1 | 6/2004 | La Rosa et al. | |
| 2004/0216190 | A1 | 10/2004 | Kovalic | |
| 2006/0057724 | A1 | 3/2006 | Alexandrov et al. | |
| 2006/0123505 | A1 * | 6/2006 | Kikuchi et al. | 800/278 |
| 2007/0033671 | A1 | 2/2007 | Jiang et al. | |
| 2007/0250956 | A1 | 10/2007 | Rothstein et al. | |

FOREIGN PATENT DOCUMENTS

| EP | 1033405 | 9/2000 |
| WO | WO0160860 | 8/2001 |
| WO | WO 2004/031349 | 4/2004 |
| WO | WO 2006/004955 | 1/2006 |
| WO | WO2006074547 | 7/2006 |

OTHER PUBLICATIONS

U.S. Appl. No. 09/729,821, filed Jun. 6, 2002, Ajinomoto Co, Inc.
U.S. Appl. No. 09/934,455, filed Jun. 26, 2003, Luc Adam et al.
Bi, Yong-mei et al, Genetic analysis of *Arabidopsis* GATA transcription factor gene family reveals a nitrate-inducible member important for chlorophyll synthesis and glucose sensitivity, the Plant Journal, 2005, pp. 680-692, vol. 44.
Butaye, "Approaches to Minimize Variation of Transgene Expression in Plants," ISB New Report, 2005.
Miura Toshihiko et al: "Flow cytometry of GATA transcription factors." Cytometry, vol. 56B, No. 1, Oct. 21, 2003, pp. 1-7, XP002507344 ISSN: 0196-4763.
Naito, T. et al Characterization of a unique GATA family gene that responds to both light and cytokinin in *Arabidopsis thaliana* Biosci. Biotechnol. Biochem. vol. 71, No. 6, Jun. 2007, pp. 1557-1560, XP008122700.
Nguyen, M. et al, Genbank Acession No. AY065074 and AAL38250, Dec. 10, 2001.
Nishii et al (Biosci. Biotechnol. Biochem. 64(7): 1402-1409, 2000).
Reyes, J.C. et al, The GATA Family of Transcription Factors in *Arabidopsis* and rice, Plant Physiology, Apr. 2004, pp. 1718-1732, vol. 34.
Scazzocchio (Cur. Opin Microbiol 3:126-131, 2000).
Town, C.D. et al, Genbank Accession No. NM_125069 and NP_200497.1, Feb. 19, 2004.
International Search Report dated Sep. 2, 2008 issued in corresponding International Application No. PCT/CA2008/000688.
International Search Report dated May 23, 2006 issued in corresponding International Application No. PCT/CA2006/000037.
GenBank, Kikuchi S. et al—AK099607, Dec. 4, 2008.
At4g26150, GenBank Accession No. NM-11874, 2011.
At5g56860, GenBank Accession No. BT025970, 2006.
J023034D16, GenBank Accession No. AK069851, 2008.
Coruzzi et al., "Nitrogen and carbon nutrient and metabolite signaling in plants," Plant Physiology 125:61-64 (2001).
Coruzzi et al., "Carbon and nitrogen sensing and signaling in plants: emerging 'matrix effects'," Current Opin. Plant Biol.4:247-253 (2001).
Riechmann et al., "Arabidopsis Transcription Factors: Genome-Wide Comparative Analysis Among Eukaryotes," Science 290:2105-2110 (2000).
Rolland et al., "Sugar sensing and signaling in plants," Plant Cell S185-S205 (2002).
Scheible et al., "Genome-Wide Reprogramming of Primary and Secondary Metabolism, Protein Synthesis, Cellular Growth Processes, and the Regulatory Infrastructure of Arabidopsis in Response to Nitrogen," Plant Physic!. 136:2483-2499 (2004).
Wang et al., "Microarray Analysis of the Nitrate Response in Arabidopsis Roots and Shoots Reveals over 1,000 Rapidly Responding Genes and New Linkages to Glucose, Trehalose-6-Phosphate, Iron, and Sulfate Metabolism," Plant Physiol., 132:556-567 (2003).
Yamaya, et al., "Genetic manipulation and quantitative-trait loci mapping for nitrogen recycling in rice," J. Exp. Bot. 53:917-925 (2002).

* cited by examiner (Continued)

*Primary Examiner* — Medina A Ibrahim
(74) *Attorney, Agent, or Firm* — Myers Bigel Sibley & Sajovec, P.A.

(57) ABSTRACT

The present invention relates to a nitrogen-regulated GATA transcription factor gene required for sugar sensing and the modulation of the expression of this gene to modulate a characteristic in a plant. The GATA transcription factor of the present invention is involved in regulating sugar sensing in plants and its expression is influenced by nitrogen status. Increased expression of this or substantially similar genes can produce plants with improved nitrogen utilization and increased yield.

16 Claims, 4 Drawing Sheets

At5g56860 full length CDS (1197 bp): SEQ ID NO. 1

```
   1 ATGGATTCAA ATTTTCATTA CTCGATAGAT CTTAACGAAG ATCAAAACCA
  51 TCACGAACAA CCCTTTTTCT ATCCTCTTGG ATCCTCTTCC TCGCTTCATC
 101 ATCATCATCA TCATCATCAT CATCAAGTCC CTTCTAATTC TTCATCTTCT
 151 TCTTCGTCCA TTTCATCGCT CTCCTCTTAC CTCCCTTTCT TGATCAACTC
 201 TCAAGAAGAT CAACATGTTG CCTACAACAA CACTTATCAC GCTGATCATC
 251 TCCATCTTTC TCAACCCCTC AAGGCCAAGA TGTTTGTGGC TAACGGTGGA
 301 TCATCAGCAT GCGATCACAT GGTGCCAAAG AAGGAGACAA GACTGAAACT
 351 AACGATAAGG AAAAAGATC ACGAAGACCA ACCCCATCCT CTTCATCAAA
 401 ACCCGACAAA ACCCGATTCA GACTCCGACA AGTGGTTGAT GTCCCCAAAG
 451 ATGCGGTTGA TCAAGAAAAC AATCACCAAC AATAAACAGC TCATTGATCA
 501 GACTAATAAT AATAATCATA AGAAAGTGA TCACTACCCT TTGAATCATA
 551 AGACTAATTT CGACGAGGAT CACCATGAAG ATCTTAATTT CAAGAACGTC
 601 TTGACCAGGA AGACCACGGC CGCGACCACC GAGAATCGCT ACAATACAAT
 651 CAACGAGAAC GGTTATAGTA ATAACAATGG CGTGATTAGG GTTTGTTCGG
 701 ATTGTAACAC CACCAAGACT CCTCTTTGGC GAAGTGGACC TCGAGGTCCC
 751 AAGTCTCTTT GTAACGCATG TGGTATACGG CAAAGAAAGG CAAGGCGAGC
 801 CGCTATGGCC GCGGCCGCTG CAGCCGGCGA CCAAGAGGTG GCGGTAGCGC
 851 CCCGAGTGCA ACAATTACCG CTGAAAAGA AGTTGCAAAA TAAAAAAAG
 901 AGATCAAACG GAGGGGAAAA ATACAATCAC TCTCCTCCAA TGGTGGCCAA
 951 GGCCAAAAAG TGCAAGATCA AGAGGAAGA GGAGAAGGAA ATGGAAGCGG
1001 AAACGGTTGC CGGAGATTCA GAGATCAGCA AATCTACAAC TTCTTCTAAT
1051 TCTTCGATTT CGTCAAACAA ATTTTGCTTC GATGATTTGA CAATAATGTT
1101 GAGCAAAAGC TCAGCTTATC AACAAGTGTT CCCACAAGAT GAGAAGGAGG
1151 CTGCTGTTTT GCTCATGGCT CTGTCGTATG GAATGGTTCA CGGTTGA
```

FIGURE 1

At5g56860 protein sequence (398 aa): SEQ ID NO. 2

```
  1 MDSNFHYSID LNEDQNHHEQ PFFYPLGSSS SLHHHHHHHH HQVPSNSSSS
 51 SSSISSLSSY LPFLINSQED QHVAYNNTYH ADHLHLSQPL KAKMFVANGG
101 SSACDHMVPK KETRLKLTIR KKDHEDQPHP LHQNPTKPDS DSDKWLMSPK
151 MRLIKKTITN NKQLIDQTNN NNHKESDHYP LNHKTNFDED HHEDLNFKNV
201 LTRKTTAATT ENRYNTINEN GYSNNNGVIR VCSDCNTTKT PLWRSGPRGP
251 KSLCNACGIR QRKARRAAMA AAAAGDQEV AVAPRVQQLP LKKKLQNKKK
301 RSNGGEKYNH SPPMVAKAKK CKIKEEEEKE MEAETVAGDS EISKSTTSSN
351 SSISSNKFCF DDLTIMLSKS SAYQQVFPQD EKEAAVLLMA LSYGMVHG
```

FIGURE 2

SEQ ID NO:3 Rice Orthologue
>OsGATA16_205599
ATGTCTACCATCTACATGAGTCAGCTCTCAGCTGCTCTCCCTCTCATGGAGGGGGAG
CACCACCATCACCACCAGGATCATCACCAAGGCCACTTCCAAGCCTTCTCCCTGCAG
CCTAAGGATCCCCCAGTCTTATTCCCCTTTGTGATCAGTAGAAGAAGCAGCAGCAGC
AGCCCTAGCGACAGCACCACTCTAAGCTATGGTTCAGACCATCACTTGACACAGCAG
CAGCAGCATCAGCATCAAGCCATGCTTGAGCCCCAAAATATGATTGGAGGATCATCC
GCTGGCATCTTTGCGACGCCGTTCCCGACCGTCAAGAGCATCCGCGACGACATGATC
GAGCGGTCGCAGTTCGATCCATACGATACCGAGAAGCTGCAGGCGAGCTGCGGGTTA
GCCAAGGTCGTCGCCGGCGGCAAGTGGAGCGCGGTGCCAGCGGCCAAGATGAAGATC
ACGAGGAAGATGGGTGAGCCGTCGTCCGGTGTCACTGGCGGGGCTGCGACGACGGTG
GCGCCGAAGAAGCCGAGGAGGAGGCCGGCGCAGGCGTACGAGGATCACGGCCATGGC
GGCGCCATGGGCCAAGCTTTTGGCGTGATTAGGGTGTGCTCCGACTGCAACACCACC
AAGACTCCCTTGTGGAGGAGTGGCCCGTGCGGCCCCAAGTCGCTTTGCAACGCGTGC
GGCATCAGGCAGAGGAAGGCGCGGCGGGCGATGATGGCCTCCGGACTACCAGCGTCC
CCCAACGCCGCCGGCCCCAAGGCGGCCGCACATAGCGGCGCCACAAACGCAGCCGCC
GCAGCTGCCATGGAGGAGACGGCCGAGTCCGCCACCGTCGCCCCGCCCCGGCGCCG
ACGACGAGGGGTGGTACTCTCGTCGACAGCATCGGGCTCAGCTGGAGCAAGACCCAT
GCCGCCGCCACCGCCTCCTGCAGCTTCCGGCCGTCACCGGTGGCTCCCGGCTTCGCG
GCGGCGGTGCAGGACGAGATCACTGACGCCGCCATGCTGCTCATGACGCTGTCCTGC
GGGCTTGTCCGGAGCTGA

FIGURE 3

NITROGEN-REGULATED SUGAR SENSING GENE AND PROTEIN AND MODULATION THEREOF

This is a divisional of U.S. application Ser. No. 11/331,199, filed Jan. 13, 2006, pending, which claims the benefit of U.S. Provisional Application No. 60/643,575, filed Jan. 14, 2005.

FIELD OF THE INVENTION

The present invention relates to methods of modulating agronomic traits in plants by modulating the expression of a GATA transcription factor in the plant cells. In particular the present invention relates to methods of improving nitrogen utilization in plants. The present invention also pertains to nucleic acid molecules isolated from *Arabidopsis thaliana* comprising nucleotide sequences that encode proteins that are sugar sensing and, ultimately, can modulate nitrogen uptake and overall carbon metabolism.

BACKGROUND OF THE INVENTION

Improvement of the agronomic characteristics of crop plants has been ongoing since the beginning of agriculture. Most of the land suitable for crop production is currently being used. As human populations continue to increase, improved crop varieties will be required to adequately provide our food and feed (Trewavas (2001) Plant Physiol. 125: 174-179). To avoid catastrophic famines and malnutrition, future crop cultivars will need to have improved yields with equivalent farm inputs. These cultivars will need to more effectively withstand adverse conditions such as drought, soil salinity or disease, which will be especially important as marginal lands are brought into cultivation. Finally, we will need cultivars with altered nutrient composition to enhance human and animal nutrition, and to enable more efficient food and feed processing. For all these traits, identification of the genes controlling phenotypic expression of traits of interest will be crucial in accelerating development of superior crop germplasm by conventional or transgenic means.

A number of highly-efficient approaches are available to assist identification of genes playing key roles in expression of agronomically-important traits. These include genetics, genomics, bioinformatics, and functional genomics. Genetics is the scientific study of the mechanisms of inheritance. By identifying mutations that alter the pathway or response of interest, classical (or forward) genetics can help to identify the genes involved in these pathways or responses. For example, a mutant with enhanced susceptibility to disease may identify an important component of the plant signal transduction pathway leading from pathogen recognition to disease resistance. Genetics is also the central component in improvement of germplasm by breeding. Through molecular and phenotypic analysis of genetic crosses, loci controlling traits of interest can be mapped and followed in subsequent generations. Knowledge of the genes underlying phenotypic variation between crop accessions can enable development of markers that greatly increase efficiency of the germplasm improvement process, as well as open avenues for discovery of additional superior alleles.

Genomics is the system-level study of an organism's genome, including genes and corresponding gene products—RNA and proteins. At a first level, genomic approaches have provided large datasets of sequence information from diverse plant species, including full-length and partial cDNA sequences, and the complete genomic sequence of a model plant species, *Arabidopsis thaliana*. Recently, the first draft sequence of a crop plant's genome, that of rice (*Oryza sativa*), has also become available. Availability of a whole genome sequence makes possible the development of tools for system-level study of other molecular complements, such as arrays and chips for use in determining the complement of expressed genes in an organism under specific conditions. Such data can be used as a first indication of the potential for certain genes to play key roles in expression of different plant phenotypes.

Bioinformatics approaches interface directly with first-level genomic datasets in allowing for processing to uncover sequences of interest by annotative or other means. Using, for example, similarity searches, alignments and phylogenetic analyses, bioinformatics can often identify homologs of a gene product of interest. Very similar homologs (eg. >~90% amino acid identity over the entire length of the protein) are very likely orthologs, i.e. share the same function in different organisms.

Functional genomics can be defined as the assignment of function to genes and their products. Functional genomics draws from genetics, genomics and bioinformatics to derive a path toward identifying genes important in a particular pathway or response of interest. Expression analysis, for example, uses high density DNA microarrays (often derived from genomic-scale organismal sequencing) to monitor the mRNA expression of thousands of genes in a single experiment. Experimental treatments can include those eliciting a response of interest, such as the disease resistance response in plants infected with a pathogen. To give additional examples of the use of microarrays, mRNA expression levels can be monitored in distinct tissues over a developmental time course, or in mutants affected in a response of interest. Proteomics can also help to assign function, by assaying the expression and post-translational modifications of hundreds of proteins in a single experiment.

Proteomics approaches are in many cases analogous to the approaches taken for monitoring mRNA expression in microarray experiments. Protein-protein interactions can also help to assign proteins to a given pathway or response, by identifying proteins that interact with known components of the pathway or response. For functional genomics, protein-protein interactions are often studied using large-scale yeast two-hybrid assays. Another approach to assigning gene function is to express the corresponding protein in a heterologous host, for example the bacterium *Escherichia coli*, followed by purification and enzymatic assays.

Demonstration of the ability of a gene-of-interest to control a given trait may be derived, for example, from experimental testing in plant species of interest. The generation and analysis of plants transgenic for a gene of interest can be used for plant functional genomics, with several advantages. The gene can often be both overexpressed and underexpressed ("knocked out"), thereby increasing the chances of observing a phenotype linking the gene to a pathway or response of interest. Two aspects of transgenic functional genomics help lend a high level of confidence to functional assignment by this approach. First, phenotypic observations are carried out in the context of the living plant. Second, the range of phenotypes observed can be checked and correlated with observed expression levels of the introduced transgene. Transgenic functional genomics is especially valuable in improved cultivar development. Only genes that function in a pathway or response of interest, and that in addition are able to confer a desired trait-based phenotype, are promoted as candidate genes for crop improvement efforts. In some cases, transgenic lines developed for functional genomics studies can be directly utilized in initial stages of product development.

Another approach towards plant functional genomics involves first identifying plant lines with mutations in specific genes of interest, followed by phenotypic evaluation of the consequences of such gene knockouts on the trait understudy. Such an approach reveals genes essential for expression of specific traits.

Genes identified through functional genomics can be directly employed in efforts towards germplasm improvement by transgenic means, as described above, or used to develop markers for identification of tracking of alleles-of-interest in mapping and breeding populations. Knowledge of such genes may also enable construction of superior alleles non-existent in nature, by any of a number of molecular methods.

Rapid increases in yield over the last 80 years in row crops have been due in roughly equal measure to improved genetics and improved agronomic practices. In particular, in a crop like maize, the combination of high yielding hybrids and the use of large amounts of nitrogen fertilizer have under ideal conditions allowed for yields of greater than 440 bu/acre. However, the use of large amounts of nitrogen fertilizer has negative side-effects primarily around increasing cost of this input to the farmer and cost to the environment since nitrate pollution is a major problem in many agricultural areas contributing significantly to the degradation of both fresh water and marine environments. Developing crop genetics that use nitrogen more efficiently through an understanding of the role of genotype on nitrogen use would be highly advantageous in reducing producer input costs as well as environmental load. This is particularly important for a crop like corn which is grown using a high level of nitrogen fertilizer.

Nitrogen use efficiency can be defined in several ways, although the simplest is yield/N supplied. There are two stages in this process: first, the amount of available nitrogen that is taken up, stored and assimilated into amino acids and other important nitrogenous compounds; second, the proportion of nitrogen that is partitioned to the seed, resulting in final yield. A variety of field studies have been performed on various agriculturally-important crops to study this problem (Lawlor D W et al 2001 in Lea P J, Morot-Gaudry J F, eds. Plant Nitrogen. Berlin: Springer-Verlag 343-367; Lafitte H R and Edmeades G O 1994 Field Crops Res 39, 15-25; Lawlor D W 2002 J Exp Bot. 53, 773-87; Moll R H et al 1982 Agron J 74, 562-564). These experiments have demonstrated that there is a genetic component to nitrogen use efficiency, but have not proved satisfactory in determining which genes are important for this process. In addition, corn breeders have generally not targeted the maintenance of yield under limiting nitrogen fertilizer. These types of field experiments on nitrogen use are difficult for a variety of reasons including a lack of uniformity of accessible nitrogen in a test field or between field sites under any treatment regime and the interplay of other environmental factors that make experiments difficult to interpret.

Therefore, although there is experimental evidence for genetic variation for this trait, it is difficult to make any conclusions from these experiments on what causes this variation. It should be feasible and is certainly important to develop methods to study this trait under field conditions in crop plants. However, significant progress toward identifying, understanding and manipulating important traits can be made through the use of a model system like *Arabidopsis*. At the very least, these experiments will give important clues about potential target genes to evaluate in important field crops. In addition, there are also considerable genetic and genomic resources available to study rice and this species will also be used for some of the proposed experiments as a species more similar to corn than is *Arabidopsis*.

Nitrate is the major form of available nitrogen in the field and there is an extensive body of literature on genes involved in nitrate uptake and reduction (Forde B G 2000 Biochimica et Biophysica Acta 1465, 219-235; Howift S M and Udvardi M K 2000 Biochimica et Biophysica Acta 1465, 152-170; Stitt M et al 2002 J Exp Bot. 53, 959-70) as well as on genes involved in other aspects of nitrogen metabolism (Lea P J, Morot-Gaudry J F, eds. 2001 Plant Nitrogen. Berlin; Springer-Verlag; Morot-Gaudry J F 2001 Nitrogen assimilation by plants Science Publishers Inc. NH, US). Also, it is clear that the availability of carbon metabolites is crucial for the efficient use of field nitrate and there is good experimental evidence for a linkage between carbon and nitrogen metabolism (Coruzzi G M and Zhou L 2001 Curr Opin Plant Biol. 4, 247-53). In addition, some experiments suggest that GS and GOGAT are involved in remobilizing N from senescing organs to the sink organ (Brouquisse R et al 2001 in Lea P J, Morot-Gaudry J F, eds. Plant Nitrogen. Berlin: Springer-Verlag 275-293; Yamaya T et al 2002 J Exp Bot. 53, 917-925). However, most aspects of the regulation of these genes are still unclear and there is still no notion of how this regulation affects nitrogen use efficiency.

Plants can sense levels of carbon and nitrogen metabolites and accordingly adjust growth and development. The perception mechanisms are complex regulatory networks that control gene expression to accommodate constant changes of nutrient-dependent cellular activities. Possession of a sugar-sensing mechanism enables plants to turn off photosynthesis when C-skeletons are abundant. The N-sensing mechanism enables plants to turn off nitrate uptake and reduction when levels of reduced or organic N are high (Coruzzi, G. M. & Zhou, L. (2001) Curr Opin Plant Biol. 4, 247-53).

Multiple sugar signal transduction pathways exist in plants. Glucose has emerged as a key regulator of many vital processes in photosynthetic plants such as in photosynthesis and in carbon and nitrogen metabolism (Roland, F., Moore, B. & Sheen, J. (2002) Plant Cell S185-S205). Hexokinases (HXK) are an important control point for glucose metabolism. They not only catalyze the phosphorylation of glucose but also function as a glucose sensor to interrelate nutrient, light and hormone signaling networks for controlling growth and development in response to the changing environment (Jang, J., Leon, P; Zhou, L. & Sheen, J. (1997) Plant Cell 9, 5-19; Dai, N., Schaffer, A., Petreikov, M., Shahak, Y., Giller, Y., Ratner, K., Levine, A. & Granot, D. (1999) Plant Cell 11, 1253-1266; Moore, B., Zhou, L., Rolland, F., Hall, Q., Cheng, W., Liu, Y., Hwang, I., Jones, T. & Sheen, J. (2003) Science 300, 332-336). In other organisms it has been shown that hexose transport molecules also serve as sugar sensors.

Multiple N signals and sensing pathways exist as well in plants. Plants have mechanisms to sense nitrate, the major form of nitrogen fertilizer, as a signal for inorganic N status as well as to sense metabolites derived from nitrate as signals for reduced or organic N status. Nitrate reductase (NR) and nitrite reductase (NiR) are the first two enzymes in the nitrate reduction process and their expression can be stimulated by the presence of nitrate and modulated by other physiological factors including some nitrogenous compounds, sucrose, light and hormone (Forde, B. G. (2000) Biochimica et Biophysica Acta 1465, 219-235; Howitt, S. M. & Udvardi, M. K. (2000) Biochimica et Biophysica Acta 1465, 152-170; Stift, M., Müller, M., Maft, M., Gibon, Y., Carilio, P., Morcuende, R., Scheible, W. & Krapp, A. (2002) J Exp Bot. 53, 959-970;

Lea, P. J. & Morot-Gaudry, J. F. eds. 2001 Plant Nitrogen. Berlin: Springer-Verlag; Morot-Gaudry J F 2001 Nitrogen assimilation by plants Science Publishers Inc. NH, US).

It is clear that carbon and nitrogen metabolism is closely linked and tightly regulated (Coruzzi, G. & Bush, D. R. (2001) Plant Physiol 125, 61-64). The availability of carbon metabolites is crucial for efficient nitrate utilization and the nitrogen status is very sensitive to photosynthesis. Despite increased knowledge of structural genes involved in carbon and nitrogen metabolism, trans-acting factors involved in transcriptional regulation of C/N gene expression have not been characterized.

GATA transcription factors are a group of transcriptional regulators broadly distributed in eukaryotes. The GATA DNA binding domain normally recognizes the consensus sequence WGATAR (W=T or A; R=G or A) (Lowry, J. & Atchley, W. (2000) J Mol Evol 50, 103-115). GATA motifs have been identified in the regulatory regions of many light responsive genes (Arguello-Astorga, G & Herrera-Estrella, L. (1998) Annu Rev Plant Physiol Plant Mol Biol 49, 525-555), including many genes involved in or relating to photosynthesis such as the RBCS, CAB (chlorophyll A/B binding protein) and GAP (glyceraldehyde-3-phosphate dehydrogenase) (Terzaghi, W. B. & Cashmore, A. R. (1995) Annu Rev Plant Physiol Plant Mol Biol 46, 445-474; Koch, K. E. (1996) Carbohydrate-modulated gene expression in plants. Annu Rev Plant Physiol Plant Mol Biol 47, 509-540; Jeong, M. J. & Shih, M. C. (2003) Biochem Biophys Res Commun 300, 555-562) as well as genes involved in nitrate assimilation such as nitrate reductase, nitrite reductase, and Gln synthetase (Jarai, G., Truong, H., Daniel-Vedele, F. & Marzluf, G. (1992) Curr Genet. 21, 37-41; Rastogi, R., Bate, N., Sivasankar, S & Rothstein, S. (1997) Plant Mol Biol. 34, 465-76; Oliveira, I. C. & Coruzzi, G. M. (1999) Plant Physiol 121, 301-309). Some known trans-acting regulatory proteins that globally regulate genes in N metabolism are GATA transcription factor genes. In yeast, four global nitrogen regulatory factors GLN3, NIL1, NIL2 and DAL80 are DNA-binding proteins that contain a single GATA zinc finger, recognizing the consensus motif GATA (Hofman-Bang, J. (1999) Mol Biotech 12, 35-73). In fungi, *Neurospora crassa* NIT2 (Tao Y and Marzluf G A 1999 Curr Genet. 36, 153-158) and *Aspergillus nidulans* AREA (Caddick M X Arst H N Jr Taylor L H Johnson R I Brownlee A G 1986 Cloning of the regulatory gene areA mediating nitrogen metabolite repression in *Aspergillus nidulans*. EMBO J 5, 1087-1090) are GATA transcription factor genes.

In plants, the in vivo function of GATA factors remains very poorly defined, with the *Arabidopsis* genome having 30 GATA members (Riechmann, J. L., Heard, J., Martin, G., Reuber, L., Jiang, C., Keddie, J., Adam, L., Pineda, O., Ratcliffe, O. J., Samaha, R. R., Creelman, R., Pilgrim, M., Broun, P., Zhang, J. Z., Ghandehari, D., Sherman, B. K. & Yu, G. (2000) Science 290, 2105-2110; Reyes, J. C., Muro-Pastor, M. I. & Florencio, F. J. (2004) Plant Physiol. 134, 1718-1732).

SUMMARY OF THE INVENTION

In the attempt to understand the biological function of members of the GATA transcription factor gene family, a GATA transcription factor gene was studied to understand its role in the regulation of carbon and nitrogen metabolism. The inventors have determined that the expression of the At5g56860 gene is influenced by the nitrogen status and its expression regulates the expression of genes controlling carbon metabolism as well as genes involved in other biological processes. Loss-of-function mutant plants in the At5g56860 gene resulted in reduced chlorophyll level and these plants were hypersensitive to exogenous glucose. In contrast, gain-of-function transgenic plants were less sensitive to exogenous glucose.

Sugars are central regulators of many vital processes in photosynthetic plants, such as photosynthesis and carbon and nitrogen metabolism. This regulation is achieved by regulating gene expression to either activate or repress genes involved. The mechanisms by which sugars control gene expression are not understood well. The GATA transcription factor disclosed here is involved in regulating sugar sensing and the expression of the factor itself is influenced by the change of the N status. Increased expression of this gene can produce plants with increased yield, particularly as the manipulation of sugar signaling pathways can lead to increased photosynthesis and increased nitrogen assimilation and alter source-sink relationships in seeds, tubes, roots and other storage organs.

Accordingly, the present invention relates to a method of modulating a characteristic in a plant or plant cell comprising modulating expression of a GATA transcription factor gene in the plant or plant cell. In an embodiment of the invention, the expression of the GATA transcription factor gene is modulated by administering, to the cell, an effective amount of an agent that can modulate the expression levels of a GATA transcription factor gene in the plant cell. In a further embodiment of the invention, the agent enhances the expression levels of a GATA transcription factor gene in the plant cell.

The characteristic to be modulated in the plant may be any agronomic trait of interest. In an embodiment of the invention, the characteristic is any that is affected by nitrogen, carbon and/or sulfur metabolism, biosynthesis of lipids, perception of nutrients, nutritional adaptation, electron transport and/or membrane associated energy conservation. In a further embodiment of the invention, the characteristic is selected from one or more of nitrogen utilization, yield, cell growth, reproduction, photosynthesis, nitrogen assimilation, disease resistance, differentiation, signal transduction, gene regulation, abiotic stress tolerance and nutritional composition. In a still further embodiment of the invention the modulated characteristic is an increase or improvement in one or more of nitrogen utilization, yield, cell growth, reproduction, photosynthesis, nitrogen assimilation, disease resistance, differentiation, signal transduction, gene regulation abiotic stress tolerance and nutritional composition.

In a particular embodiment, the present invention relates to a method of improving nitrogen utilization in a plant or plant cell comprising enhancing expression of a GATA transcription factor gene in the plant or plant cell. Improving nitrogen utilization in a plant will allow for reduce amounts of nitrogen fertilizer to applied to the plant with a concomitant reduction in costs to the farmer and cost to the environment since nitrate pollution is a major problem in many agricultural areas contributing significantly to the degradation of both fresh water and marine environments.

The plant or plant cell may be from any plant wherein one wishes to modulate a characteristic. In an embodiment of the invention, the plant cell is a dicot, a gymnosperm or a monocot. In one embodiment, the dicot is selected from the group consisting of soybean, tobacco or cotton. In a further embodiment of the invention, the monocot is selected from maize, wheat, barley, oats, rye, millet, sorghum, triticale, secale, einkorn, spelt, emmer, teff, milo, flax, gramma grass, *Tripsacum* sp. and teosite.

In an embodiment of the invention, the agent that enhances the expression levels of a GATA transcription factor gene in the plant cell comprises a nucleic acid molecule encoding a GATA transcription factor.

In an embodiment of the invention, the agent that can modulate the expression levels of a GATA transcription factor gene in a plant cell comprises:
(a) a nucleotide sequence of SEQ ID NO:1 or a fragment or domain thereof;
(b) a nucleotide sequence encoding a polypeptide of SEQ ID NO:2, a fragment or domain thereof;
(c) a nucleotide sequence having substantial similarity to (a) or (b);
(d) a nucleotide sequence capable of hybridizing to (a), (b) or (c);
(e) a nucleotide sequence complementary to (a), (b), (c) or (d); or
(f) a nucleotide sequence that is the reverse complement of (a), (b), (c) or (d).

In a further embodiment of the invention, the nucleic acid molecule comprises the sequence of the AT5g56860 gene of SEQ ID NO:1 or a functional fragment thereof. In a still further embodiment of the invention, the nucleic acid molecule comprises a sequence that hybridizes under medium stringency conditions to the AT5g56860 gene of SEQ ID NO:1 or a functional fragment thereof. In another embodiment of the present invention, the nucleic acid molecule is derived from the nucleotide sequence of the At5g56860 gene of SEQ ID NO:1 and has a nucleotide sequence comprising codons specific for expression in plants. In yet another embodiment of the invention, the nucleic acid molecule is the rice orthologue of the AT5g56860 gene comprising the sequence of SEQ ID NO:3.

In a further embodiment of the invention, the agent that can modulate the expression levels of a GATA transcription factor gene in a plant cell comprises:
(a) a polypeptide sequence listed in SEQ ID NO:2, or a functional fragment, domain, repeat, or chimera thereof;
(b) a polypeptide sequence having substantial similarity to (a);
(c) a polypeptide sequence encoded by a nucleotide sequence identical to or having substantial similarity to a nucleotide sequence listed in SEQ ID NO:1, or a functional fragment or domain thereof, or a sequence complementary thereto; or
(d) a polypeptide sequence encoded by a nucleotide sequence capable of hybridizing under medium stringency conditions to a nucleotide sequence listed in SEQ ID NO:1, or to a sequence complementary thereto.

In an embodiment of the present invention, when the agent is a nucleic acid sequence, the nucleic acid sequence is expressed in a specific location or tissue of the plant. The location or tissue is for example, but not limited to, epidermis, root, vascular tissue, meristem, cambium, cortex, pith, leaf and/or flower. In an alternative embodiment, the location or tissue is a seed.

Embodiments of the present invention also relate to use of a shuffled nucleic acid molecule for modulating a characteristic in a plant cell, said shuffled nucleic acid molecule containing a plurality of nucleotide sequence fragments, wherein at least one of the fragments encodes a GATA transcription factor and wherein at least two of the plurality of sequence fragments are in an order, from 5' to 3' which is not an order in which the plurality of fragments naturally occur in a nucleic acid. In a specific embodiment, all of the fragments in a shuffled nucleic acid molecule containing a plurality of nucleotide sequence fragments are from a single gene. In a more specific embodiment, the plurality of fragments originate from at least two different genes. In a more specific embodiment, the shuffled nucleic acid is operably linked to a promoter sequence. Another more specific embodiment is a use of a chimeric polynucleotide for modulating a characteristic in a plant cell, said chimeric polynucleotide including a promoter sequence operably linked to the shuffled nucleic acid. In a more specific embodiment, the shuffled nucleic acid is contained within a host cell. In a further specific embodiment of the invention the fragment encoding a GATA transcription factor consists of or comprises:
(a) a nucleotide sequence of SEQ ID NO:1 or a fragment or domain thereof;
(b) a nucleotide sequence encoding a polypeptide of SEQ ID NO:2, a fragment or domain thereof;
(c) a nucleotide sequence having substantial similarity to (a) or (b);
(d) a nucleotide sequence capable of hybridizing to (a), (b) or (c);
(e) a nucleotide sequence complementary to (a), (b), (c) or (d); or
(f) a nucleotide sequence that is the reverse complement of (a), (b), (c) or (d).

Embodiments of the present invention also contemplate a use of an expression cassette for modulating a characteristic in a plant cell including a promoter sequence operably linked to an isolated nucleic acid encoding a GATA transcription factor. In embodiments of the invention the isolated nucleic acid encoding a GATA transcription factor consists of or comprises:
(a) a nucleotide sequence of SEQ ID NO:1 or a fragment or domain thereof;
(b) a nucleotide sequence encoding a polypeptide of SEQ ID NO:2, a fragment or domain thereof;
(c) a nucleotide sequence having substantial similarity to (a) or (b);
(d) a nucleotide sequence capable of hybridizing to (a), (b) or (c)
(e) a nucleotide sequence complementary to (a), (b), (c) or (d); or
(f) a nucleotide sequence that is the reverse complement of (a), (b), (c) or (d).

Further encompassed within the invention is use of a recombinant vector for modulating a characteristic in a plant cell comprising an expression cassette including a promoter sequence operably linked to an isolated nucleic acid encoding a GATA transcription factor. In embodiments of the invention the isolated nucleic acid encoding a GATA transcription factor consists of or comprises:
(a) a nucleotide sequence of SEQ ID NO:1 or a fragment or domain thereof;
(b) a nucleotide sequence encoding a polypeptide of SEQ ID NO:2, a fragment or domain thereof;
(c) a nucleotide sequence having substantial similarity to (a) or (b);
(d) a nucleotide sequence capable of hybridizing to (a), (b) or (c)
(e) a nucleotide sequence complementary to (a), (b), (c) or (d); or
(f) a nucleotide sequence that is the reverse complement of (a), (b), (c) or (d).

Also encompassed are uses of plant cells, which contain expression cassettes, according to the present disclosure, and uses of plants, containing these plant cells.

In one embodiment, the expression cassette is expressed throughout the plant. In another embodiment the expression cassette is expressed in a specific location or tissue of a plant.

In a specific embodiment, the location or tissue may be, for example, epidermis, root, vascular tissue, meristem, cambium, cortex, pith, leaf, and flower. In an alternative specific embodiment, the location or tissue is a seed.

Embodiments of the present invention also provide the use of seed and isolated product from plants for modulating a characteristic in a plant cell, which contain an expression cassette including a promoter sequence operably linked to an isolated nucleic acid encoding a GATA transcription factor gene according to the present invention.

In a specific embodiment, the expression vector includes one or more elements such as, for example, but not limited to, a promoter-enhancer sequence, a selection marker sequence, an origin of replication, an epitope-tag encoding sequence, or an affinity purification-tag encoding sequence. In a more specific embodiment, the promoter-enhancer sequence may be, for example, the CaMV 35S promoter, the CaMV 19S promoter, the tobacco PR-1a promoter, ubiquitin and the phaseolin promoter. In another embodiment, the promoter is operable in plants, and more specifically, a constitutive or inducible promoter. In another specific embodiment, the selection marker sequence encodes an antibiotic resistance gene. In another specific embodiment, the epitope-tag sequence encodes V5, the peptide Phe-His-His-Thr-Thr, hemagglutinin, or glutathione-S-transferase. In another specific embodiment the affinity purification-tag sequence encodes a polyamino acid sequence or a polypeptide. In a more specific embodiment, the polyamino acid sequence is polyhistidine. In a more specific embodiment, the polypeptide is chitin binding domain or glutathione-S-transferase. In a more specific embodiment, the affinity purification-tag sequence comprises an intein encoding sequence.

In a specific embodiment, the expression vector is a eukaryotic expression vector or a prokaryotic expression vector. In a more specific embodiment, the eukaryotic expression vector includes a tissue-specific promoter. More specifically, the expression vector is operable in plants.

Embodiments of the present invention also relate to a plant modified by a method that includes introducing into a plant a nucleic acid where the nucleic acid is expressible in the plant in an amount effective to effect the modification. The modification can be an increase or decrease in the one or more traits of interest. The modification may include overexpression, underexpression, antisense modulation, sense suppression, inducible expression, inducible repression, or inducible modulation of a gene. In an embodiment of the invention the modification involved an increase or improvement in the trait of interest, for example, nitrogen utilization.

Embodiments of the present invention provide nucleotide and amino acid sequences isolated from *Arabidopsis thaliana*. Particularly, the present invention relates to a nitrogen-regulated GATA transcription factor gene required for sugar sensing.

Embodiments of the present invention relate to an isolated nucleic acid comprising or consisting of a nucleotide sequence comprising:

(a) a nucleotide sequence listed in SEQ ID NO:1, or a fragment or domain, thereof;
(b) a nucleotide sequence having substantial similarity to (a);
(c) a nucleotide sequence capable of hybridizing to (a);
(d) a nucleotide sequence complementary to (a), (b) or (c); or
(e) a nucleotide sequence which is the reverse complement of (a), (b) or (c).

In a specific embodiment, the substantial similarity is at least about 65% identity, specifically about 80% identity, specifically 90%, and more specifically at least about 95% sequence identity to the nucleotide sequence listed as SEQ ID NO:1, a fragment or domain thereof.

In a one embodiment the sequence having substantial similarity to the nucleotide sequence of SEQ ID NO:1, a fragment or domain thereof, is from a plant. In a specific embodiment, the plant is a dicot. In a more specific embodiment, the dicot is selected from the group consisting of soybean, tobacco or cotton. In another specific embodiment, the plant is a gymnosperm. In another specific embodiment, the plant is a monocot. In a more specific embodiment, the monocot is a cereal. In a more specific embodiment, the cereal may be, for example, maize, wheat, barley, oats, rye, millet, sorghum, triticale, secale, einkorn, spelt, emmer, teff, milo, flax, gramma grass, *Tripsacum* sp., or teosinte.

In one embodiment the nucleic acid is expressed in a specific location or tissue of a plant. The location or tissue is for example, but not limited to, epidermis, root, vascular tissue, meristem, cambium, cortex, pith, leaf, and flower. In an alternative embodiment, the location or tissue is a seed. In another embodiment, the nucleic acid encodes a polypeptide involved in a function such as, for example, but not limited to, carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation.

In a specific embodiment, the isolated nucleic acid comprises or consists of a nucleotide sequence capable of hybridizing to a nucleotide sequence listed in SEQ ID NO:1 or a fragment or domain thereof. In a specific embodiment, hybridization allows the sequence to form a duplex at medium or high stringency. Embodiments of the present invention also encompass a nucleotide sequence complementary to a nucleotide sequence of SEQ ID NO:1 or a fragment or domain thereof. Embodiments of the present invention further encompass a nucleotide sequence complementary to a nucleotide sequence that has substantial similarity or is capable of hybridizing to a nucleotide sequence of SEQ ID NO:1 or a fragment or domain thereof.

In a specific embodiment, the nucleotide sequence having substantial similarity is an allelic variant of the nucleotide sequence of SEQ ID NO:1 a fragment or domain thereof. In an alternate embodiment, the sequence having substantial similarity is a naturally occurring variant. In another alternate embodiment, the sequence having substantial similarity is a polymorphic variant of the nucleotide sequence of SEQ ID NO:1 or a fragment or domain thereof.

In a specific embodiment, the isolated nucleic acid contains a plurality of regions having the nucleotide sequence of SEQ ID NO:1 or exon or domain thereof.

In a specific embodiment, the isolated nucleic acid contains a polypeptide-encoding sequence. In a more specific embodiment, the polypeptide-encoding sequence contains a 20 base pair nucleotide portion identical in sequence to a consecutive 20 base pair nucleotide portion of a nucleic acid sequence of SEQ ID NO:1. In a more specific embodiment, the polypeptide contains a polypeptide sequence of SEQ ID NO:2, or a fragment thereof. In a more specific embodiment, the polypeptide is a plant polypeptide. In a more specific embodiment, the plant is a dicot. In a more specific embodiment, the plant is a gymnosperm. In a more specific embodiment, the plant is a monocot. In a more specific embodiment, the monocot is a cereal. In a more specific embodiment, the cereal may be, for example, maize, wheat, barley, oats, rye, millet, sorghum, triticale, secale, einkorn, spelt, emmer, teff, miloflax, gramma grass, *Tripsacum*, and teosinte.

In one embodiment, the polypeptide is expressed throughout the plant. In a more specific embodiment, the polypeptide is expressed in a specific location or tissue of a plant. In a more specific embodiment, the location or tissue may be, for example, epidermis, root, vascular tissue, meristem, cambium, cortex, pith, leaf, and flower. In a most specific embodiment, the location or tissue is a seed.

In a specific embodiment, the sequence of the isolated nucleic acid encodes a polypeptide useful for generating an antibody having immunoreactivity against a polypeptide encoded by a nucleotide sequence of SEQ ID NO:2, or fragment or domain thereof.

In a specific embodiment, the sequence having substantial similarity contains a deletion or insertion of at least one nucleotide. In a more specific embodiment, the deletion or insertion is of less than about thirty nucleotides. In a most specific embodiment, the deletion or insertion is of less than about five nucleotides.

In a specific embodiment, the sequence of the isolated nucleic acid having substantial similarity comprises or consists of a substitution in at least one codon. In a specific embodiment, the substitution is conservative.

Embodiments of the present invention also relate to an isolated nucleic acid molecule comprising or consisting of a nucleotide sequence, its complement, or its reverse complement, encoding a polypeptide including:
(a) a polypeptide sequence of SEQ ID NO:2, or a fragment, domain, repeat, or chimera thereof;
(b) a polypeptide sequence having substantial similarity to (a);
(c) a polypeptide sequence encoded by a nucleotide sequence identical to or having substantial similarity to a nucleotide sequence of SEQ ID NO:1, or a fragment or domain thereof, or a sequence complementary thereto;
(d) a polypeptide sequence encoded by a nucleotide sequence capable of hybridizing under medium stringency conditions to a nucleotide sequence of SEQ ID NO:1 or a sequence complementary thereto; or
(e) a functional fragment of (a), (b), (c) or (d).

In another specific embodiment, the polypeptide having substantial similarity is an allelic variant of a polypeptide sequence of SEQ ID NO:2, or a fragment, domain, repeat or chimera thereof. In another specific embodiment, the isolated nucleic acid includes a plurality of regions from the polypeptide sequence encoded by a nucleotide sequence identical to or having substantial similarity to a nucleotide sequence of SEQ ID NO:1, or fragment or domain thereof, or a sequence complementary thereto.

In another specific embodiment, the polypeptide is a polypeptide sequence of SEQ ID NO:2. In another specific embodiment, the polypeptide is a functional fragment or domain. In yet another specific embodiment, the polypeptide is a chimera, where the chimera may include functional protein domains, including domains, repeats, post-translational modification sites, or other features. In a more specific embodiment, the polypeptide is a plant polypeptide. In a more specific embodiment, the plant is a dicot. In a more specific embodiment, the plant is a gymnosperm. In a more specific embodiment, the plant is a monocot. In a more specific embodiment, the monocot is a cereal. In a more specific embodiment, the cereal may be, for example, maize, wheat, barley, oats, rye, millet, sorghum, triticale, secale, einkorn, spelt, emmer, teff, milo, flax, gramma grass, *Tripsacum*, and teosinte.

In a specific embodiment, the polypeptide is expressed in a specific location or tissue of a plant. In a more specific embodiment, the location or tissue may be, for example, epidermis, root, vascular tissue, meristem, cambium, cortex, pith, leaf, and flower. In another specific embodiment, the location or tissue is a seed.

In a specific embodiment, the polypeptide sequence encoded by a nucleotide sequence having substantial similarity to a nucleotide sequence of SEQ ID NO:1 or a fragment or domain thereof or a sequence complementary thereto, includes a deletion or insertion of at least one nucleotide. In a more specific embodiment, the deletion or insertion is of less than about thirty nucleotides. In a most specific embodiment, the deletion or insertion is of less than about five nucleotides.

In a specific embodiment, the polypeptide sequence encoded by a nucleotide sequence having substantial similarity to a nucleotide sequence of SEQ ID NO:1, or a fragment or domain thereof or a sequence complementary thereto, includes a substitution of at least one codon. In a more specific embodiment, the substitution is conservative.

In a specific embodiment, the polypeptide sequences having substantial similarity to the polypeptide sequence of SEQ ID NO:2 or a fragment, domain, repeat, or chimeras thereof includes a deletion or insertion of at least one amino acid.

In a specific embodiment, the polypeptide sequences having substantial similarity to the polypeptide sequence of SEQ ID NO:2 or a fragment, domain, repeat, or chimeras thereof includes a substitution of at least one amino acid.

Embodiments of the present invention also relate to a shuffled nucleic acid containing a plurality of nucleotide sequence fragments, wherein at least one of the fragments corresponds to a region of a nucleotide sequence of SEQ ID NO:1 and wherein at least two of the plurality of sequence fragments are in an order, from 5' to 3' which is not an order in which the plurality of fragments naturally occur in a nucleic acid. In a more specific embodiment, all of the fragments in a shuffled nucleic acid containing a plurality of nucleotide sequence fragments are from a single gene. In a more specific embodiment, the plurality of fragments originates from at least two different genes. In a more specific embodiment, the shuffled nucleic acid is operably linked to a promoter sequence. Another more specific embodiment is a chimeric polynucleotide including a promoter sequence operably linked to the shuffled nucleic acid. In a more specific embodiment, the shuffled nucleic acid is contained within a host cell.

Embodiments of the present invention also contemplate an expression cassette including a promoter sequence operably linked to an isolated nucleic acid containing a nucleotide sequence including:
a) a nucleotide sequence of SEQ ID NO:1 or a fragment or domain thereof;
(b) a nucleotide sequence encoding a polypeptide of SEQ ID NO:2, a fragment or domain thereof;
(c) a nucleotide sequence having substantial similarity to (a) or (b);
(d) a nucleotide sequence capable of hybridizing to (a), (b) or (c);
(e) a nucleotide sequence complementary to (a), (b), (c) or (d); or
(f) a nucleotide sequence that is the reverse complement of (a), (b), (c) or (d).

Further encompassed within the invention is a recombinant vector comprising an expression cassette according to embodiments of the present invention. Also encompassed are plant cells, which contain expression cassettes, according to the present disclosure, and plants, containing these plant cells. In a specific embodiment, the plant is a dicot. In a more specific embodiment, the dicot is selected from the group consisting of soybean, tobacco or cotton. In another specific embodiment, the plant is a gymnosperm. In another specific embodiment, the plant is a monocot. In a more specific embodiment, the monocot is a cereal. In a more specific embodiment, the cereal may be, for example, maize, wheat, barley, oats, rye, millet, sorghum, triticale, secale, einkorn, spelt, emmer, teff, milo, flax, gramma grass, *Tripsacum* and teosinte.

In one embodiment, the expression cassette is expressed throughout the plant. In another embodiment, the expression cassette is expressed in a specific location or tissue of a plant. In a specific embodiment, the location or tissue may be, for example, epidermis, root, vascular tissue, meristem, cambium, cortex, pith, leaf, and flower. In an alternative specific embodiment, the location or tissue is a seed.

In one embodiment, the expression cassette is involved in a function such as, for example, but not limited to, carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation. In a more specific embodiment, the chimeric polypeptide is involved in a function such as, nitrogen utilization, abiotic stress tolerance, enhanced yield, disease resistance and/or nutritional composition.

In one embodiment, the plant contains a modification to a phenotype or measurable characteristic of the plant, the modification being attributable to the expression of at least one gene contained in the expression cassette. In a specific embodiment, the modification may be, for example, carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation.

Embodiments of the present invention also provide seed and isolated product from plants which contain an expression cassette including a promoter sequence operably linked to an isolated nucleic acid containing a nucleotide sequence including:
(a) a nucleotide sequence of SEQ ID NO:1 or a fragment or domain thereof;
(b) a nucleotide sequence encoding a polypeptide of SEQ ID NO:2, a fragment or domain thereof;
(c) a nucleotide sequence having substantial similarity to (a) or (b);
(d) a nucleotide sequence capable of hybridizing to (a), (b) or (c);
(e) a nucleotide sequence complementary to (a), (b), (c) or (d); or
(f) a nucleotide sequence that is the reverse complement of (a), (b), (c) or (d) according to the present disclosure.

In a specific embodiment the isolated product includes an enzyme, a nutritional protein, a structural protein, an amino acid, a lipid, a fatty acid, a polysaccharide, a sugar, an alcohol, an alkaloid, a carotenoid, a propanoid, a steroid, a pigment, a vitamin and a plant hormone.

Embodiments of the present invention also relate to isolated products produced by expression of an isolated nucleic acid containing a nucleotide sequence including:
(a) a nucleotide sequence of SEQ ID NO:1, or fragment or domain thereof;
(b) a nucleotide sequence encoding a polypeptide of SEQ ID NO:2, or a fragment or domain thereof;
(c) a nucleotide sequence having substantial similarity to (a) or (b);
(d) a nucleotide sequence capable of hybridizing to (a) or (b);
(e) a nucleotide sequence complementary to (a), (b), (c) or (d); or
(f) a nucleotide sequence that is the reverse complement of (a), (b) (c) or (d) according to the present disclosure.

In a specific embodiment, the product is produced in a plant. In another specific embodiment, the product is produced in cell culture. In another specific embodiment, the product is produced in a cell-free system. In another specific embodiment, the product includes an enzyme, a nutritional protein, a structural protein, an amino acid, a lipid, a fatty acid, a polysaccharide, a sugar, an alcohol, an alkaloid, a carotenoid, a propanoid, a steroid, a pigment, a vitamin and a plant hormone.

In a specific embodiment, the product is a polypeptide containing an amino acid sequence of SEQ ID NO:2. In a more specific embodiment, the protein is an transcription factor.

Embodiments of the present invention further relate to an isolated polynucleotide including a nucleotide sequence of at least 10 bases, which sequence is identical, complementary, or substantially similar to a region of any sequence of SEQ ID NO:1, and wherein the polynucleotide is adapted for any of numerous uses.

In a specific embodiment, the polynucleotide is used as a chromosomal marker. In another specific embodiment, the polynucleotide is used as a marker for RFLP analysis. In another specific embodiment, the polynucleotide is used as a marker for quantitative trait linked breeding. In another specific embodiment, the polynucleotide is used as a marker for marker-assisted breeding. In another specific embodiment, the polynucleotide is used as a bait sequence in a two-hybrid system to identify sequence-encoding polypeptides interacting with the polypeptide encoded by the bait sequence. In another specific embodiment, the polynucleotide is used as a diagnostic indicator for genotyping or identifying an individual or population of individuals. In another specific embodiment, the polynucleotide is used for genetic analysis to identify boundaries of genes or exons.

Embodiments of the present invention also relate to an expression vector comprising or consisting of a nucleic acid molecule including:
(a) a nucleic acid encoding a polypeptide as listed in SEQ ID NO:2
(b) a fragment, one or more domains, or featured regions of SEQ ID NO:1; or
(c) a complete nucleic acid sequence listed in SEQ ID NO:1, or a fragment thereof, in combination with a heterologous sequence.

In a specific embodiment, the expression vector includes one or more elements such as, for example, but not limited to, a promoter-enhancer sequence, a selection marker sequence, an origin of replication, an epitope-tag encoding sequence, or an affinity purification-tag encoding sequence. In a more specific embodiment, the promoter-enhancer sequence may be, for example, the CaMV 35S promoter, the CaMV 19S promoter, the tobacco PR-1a promoter, ubiquitin and the phaseolin promoter. In another embodiment, the promoter is operable in plants, and more specifically, a constitutive or inducible promoter. In another specific embodiment, the selection marker sequence encodes an antibiotic resistance gene. In another specific embodiment, the epitope-tag sequence encodes V5, the peptide Phe-His-His-Thr-Thr, hemagglutinin, or glutathione-S-transferase. In another specific embodiment the affinity purification-tag sequence encodes a polyamino acid sequence or a polypeptide. In a more specific embodiment, the polyamino acid sequence is polyhistidine. In a more specific embodiment, the polypeptide is chitin binding domain or glutathione-S-transferase. In a more specific embodiment, the affinity purification-tag sequence comprises an intein encoding sequence.

In a specific embodiment, the expression vector is a eukaryotic expression vector or a prokaryotic expression vector. In a more specific embodiment, the eukaryotic expression vector includes a tissue-specific promoter. More specifically, the expression vector is operable in plants.

Embodiments of the present invention also relate to a cell comprising or consisting of a nucleic acid construct comprising an expression vector and a nucleic acid including a nucleic acid encoding a polypeptide as listed in SEQ ID NO:2, or a nucleic acid sequence listed in SEQ ID NO:1, or a segment thereof, in combination with a heterologous sequence.

In a specific embodiment, the cell is a bacterial cell, a fungal cell, a plant cell, or an animal cell. In a specific embodiment, the cell is a plant cell. In a more specific embodiment, the polypeptide is expressed in a specific location or tissue of a plant. In a most specific embodiment, the location or tissue may be, for example, epidermis, root, vascular tissue, meristem, cambium, cortex, pith, leaf, and flower. In an alternate most specific embodiment, the location or tissue is a seed. In a specific embodiment, the polypeptide is involved in a function such as, for example, carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation.

Embodiments of the present invention also relate to polypeptides encoded by the isolated nucleic acid molecules of the present disclosure including a polypeptide containing a polypeptide sequence encoded by an isolated nucleic acid containing a nucleotide sequence including:
(a) a nucleotide sequence listed in SEQ ID NO:1 or an exon or domain thereof;
(b) a nucleotide sequence having substantial similarity to (a);
(c) a nucleotide sequence capable of hybridizing to (a);
(d) a nucleotide sequence complementary to (a), (b) or (c); or
(e) a nucleotide sequence which is the reverse complement of (a), (b) or (c);
(f) or a functional fragment thereof.

A polypeptide containing a polypeptide sequence encoded by an isolated nucleic acid containing a nucleotide sequence, its complement, or its reverse complement, encoding a polypeptide including a polypeptide sequence including:
(a) a polypeptide sequence listed in SEQ ID NO:2, or a domain, repeat, or chimeras thereof;
(b) a polypeptide sequence having substantial similarity to (a);
(c) a polypeptide sequence encoded by a nucleotide sequence identical to or having substantial similarity to a nucleotide sequence listed SEQ ID NO:1, or an exon or domain thereof, or a sequence complementary thereto;
(d) a polypeptide sequence encoded by a nucleotide sequence capable of hybridizing under medium stringency conditions to a nucleotide sequence listed in SEQ ID NO:1 or to a sequence complementary thereto; or
(e) a functional fragment of (a), (b), (c) or (d);
(f) or a functional fragment thereof.

Embodiments of the present invention contemplate a polypeptide containing a polypeptide sequence encoded by an isolated nucleic acid which includes a shuffled nucleic acid containing a plurality of nucleotide sequence fragments, wherein at least one of the fragments corresponds to a region of a nucleotide sequence listed SEQ ID NO:1, and wherein at least two of the plurality of sequence fragments are in an order, from 5' to 3' which is not an order in which the plurality of fragments naturally occur in a nucleic acid, or functional fragment thereof.

Embodiments of the present invention contemplate a polypeptide containing a polypeptide sequence encoded by an isolated polynucleotide containing a nucleotide sequence of at least 10 bases, which sequence is identical, complementary, or substantially similar to a region of any of sequences of SEQ ID NO:1, or functional fragment thereof and wherein the polynucleotide is adapted for a use including:
(a) use as a chromosomal marker to identify the location of the corresponding or complementary polynucleotide on a native or artificial chromosome;
(b) use as a marker for RFLP analysis;
(c) use as a marker for quantitative trait linked breeding;
(d) use as a marker for marker-assisted breeding;
(e) use as a bait sequence in a two-hybrid system to identify sequence encoding polypeptides interacting with the polypeptide encoded by the bait sequence;
(f) use as a diagnostic indicator for genotyping or identifying an individual or population of individuals; or
(g) use for genetic analysis to identify boundaries of genes or exons.

Embodiments of the present invention also contemplate an isolated polypeptide containing a polypeptide sequence including:
(a) a polypeptide sequence listed SEQ ID NO:2, or exon or domain thereof;
(b) a polypeptide sequence having substantial similarity to (a);
(c) a polypeptide sequence encoded by a nucleotide sequence identical to or having substantial similarity to a nucleotide sequence SEQ ID NO:1, or an exon or domain thereof or a sequence complementary thereto;
(d) a polypeptide sequence encoded by a nucleotide sequence capable of hybridizing under medium stringency conditions to a nucleotide sequence listed in SEQ ID NO:1, or to a sequence complementary thereto; or
(e) a functional fragment of (a), (b), (c) or (d).

In a specific embodiment, the substantial similarity is at least about 65% identity. In a more specific embodiment, the substantial similarity is at least about 80% identity. In a most specific embodiment, the substantial similarity is at least about 95% identity. In a specific embodiment, the substantial similarity is at least three percent greater than the percent identity to the closest homologous sequence listed in any of the Sequence Listings.

In a specific embodiment, the sequence having substantial similarity is from a plant. In a more specific embodiment, the plant is a dicot. In a more specific embodiment, the plant is a gymnosperm. In a more specific embodiment, the plant is a monocot. In a more specific embodiment, the monocot is a cereal. In a more specific embodiment, the cereal may be, for example, maize, wheat, barley, oats, rye, millet, sorghum, triticale, secale, einkorn, spelt, emmer, teff, milo, flax, gramma grass, *Tripsacum* and teosinte.

In a specific embodiment, the polypeptide is expressed in a specific location or tissue of a plant. In a more specific embodiment, the location or tissue may be, for example, epidermis, root, vascular tissue, meristem, cambium, cortex, pith, leaf, and flower. In another specific embodiment, the location or tissue is a seed. In a specific embodiment, the polypeptide is involved in a function such as, for example, carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation.

In a specific embodiment, hybridization of a polypeptide sequence encoded by a nucleotide sequence identical to or having substantial similarity to a nucleotide sequence listed in SEQ ID NO:1, or an exon or domain thereof, or a sequence complementary thereto, or a polypeptide sequence encoded by a nucleotide sequence capable of hybridizing under medium stringency conditions to a nucleotide sequence listed SEQ ID NO:1, or to a sequence complementary thereto, allows the sequence to form a duplex at medium or high stringency.

In a specific embodiment, a polypeptide having substantial similarity to a polypeptide sequence listed in SEQ ID NO:2, or exon or domain thereof, is an allelic variant of the polypeptide sequence listed in SEQ ID NO:2. In another specific embodiment, a polypeptide having substantial similarity to a polypeptide sequence listed in SEQ ID NO:2, or exon or domain thereof is a naturally occurring variant of the polypeptide sequence listed in SEQ ID NO:2. In another specific embodiment, a polypeptide having substantial similarity to a polypeptide sequence listed in SEQ ID NO:2, or exon or domain thereof is a polymorphic variant of the polypeptide sequence listed in SEQ ID NO:2.

In an alternate specific embodiment, the sequence having substantial similarity contains a deletion or insertion of at least one amino acid. In a more specific embodiment, the deletion or insertion is of less than about ten amino acids. In a most specific embodiment, the deletion or insertion is of less than about three amino acids.

In a specific embodiment, the sequence having substantial similarity encodes a substitution in at least one amino acid.

Also contemplated is a method of producing a plant comprising a modification thereto, including the steps of: (1) providing a nucleic acid which is an isolated nucleic acid containing a nucleotide sequence including:
  (a) a nucleotide sequence listed SEQ ID NO:1, or exon or domain thereof;
  (b) a nucleotide sequence having substantial similarity to (a);
  (c) a nucleotide sequence capable of hybridizing to (a);
  (d) a nucleotide sequence complementary to (a), (b) or (c); or
  (e) a nucleotide sequence which is the reverse complement of (a), (b) or (c);
and (2) introducing the nucleic acid into the plant, wherein the nucleic acid is expressible in the plant in an amount effective to effect the modification. In one embodiment, the modification comprises an altered characteristic in the plant, wherein the characteristic corresponds to the nucleic acid introduced into the plant. In other specific embodiments the characteristic corresponds to carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation.

In another embodiment, the modification includes an increased or decreased expression or accumulation of a product of the plant. Specifically, the product is a natural product of the plant. Equally specifically, the product is a new or altered product of the plant. Specifically, the product comprises a GATA transcription factor.

Also encompassed within the presently disclosed invention is a method of producing a recombinant protein, comprising the steps of:

(a) growing recombinant cells comprising a nucleic acid construct under suitable growth conditions, the construct comprising an expression vector and a nucleic acid including: a nucleic acid encoding a protein as listed in SEQ ID NO:2, or a nucleic acid sequence listed in SEQ ID NO:1, or segments thereof; and
  (b) isolating from the recombinant cells the recombinant protein expressed thereby.

Embodiments of the present invention provide a method of producing a recombinant protein in which the expression vector includes one or more elements including a promoter-enhancer sequence, a selection marker sequence, an origin of replication, an epitope-tag encoding sequence, and an affinity purification-tag encoding sequence. In one specific embodiment, the nucleic acid construct includes an epitope-tag encoding sequence and the isolating step includes use of an antibody specific for the epitope-tag. In another specific embodiment, the nucleic acid construct contains a polyamino acid encoding sequence and the isolating step includes use of a resin comprising a polyamino acid binding substance, specifically where the polyamino acid is polyhistidine and the polyamino binding resin is nickel-charged agarose resin in yet another specific embodiment, the nucleic acid construct contains a polypeptide encoding sequence and the isolating step includes the use of a resin containing a polypeptide binding substance, specifically where the polypeptide is a chitin binding domain and the resin contains chitin-sepharose.

Embodiments of the present invention also relate to a plant modified by a method that includes introducing into a plant a nucleic acid where the nucleic acid is expressible in the plant in an amount effective to effect the modification. The modification can be, for example, carbon, nitrogen and/or sulfur metabolism, nitrogen utilization, nitrogen assimilation, photosynthesis, signal transduction, cell growth, reproduction, disease resistance, abiotic stress tolerance, nutritional composition, gene regulation, and/or differentiation. In one embodiment, the modified plant has increased or decreased resistance to an herbicide, a stress, or a pathogen. In another embodiment, the modified plant has enhanced or diminished requirement for light, water, nitrogen, or trace elements. In yet another embodiment, the modified plant is enriched for an essential amino acid as a proportion of a protein fraction of the plant. The protein fraction may be, for example, total seed protein, soluble protein, insoluble protein, water-extractable protein, and lipid-associated protein. The modification may include overexpression, underexpression, antisense modulation, sense suppression, inducible expression, inducible repression, or inducible modulation of a gene.

The invention further relates to a seed from a modified plant or an isolated product of a modified plant, where the product may be an enzyme, a nutritional protein, a structural protein, an amino acid, a lipid, a fatty acid, a polysaccharide, a sugar, an alcohol, an alkaloid, a carotenoid, a propanoid, a steroid, a pigment, a vitamin and a plant hormone.

The above Summary of Invention lists several embodiments of the invention, and in many cases lists variations and permutations of these embodiments. The Summary is merely exemplary of the numerous and varied embodiments Mention of one or more specific features of a given embodiment is likewise exemplary. Such embodiment can typically exist with or without the feature(s) mentioned; likewise, those features can be applied to other embodiments of the invention, whether listed in this Summary or not. To avoid excessive repetition, this Summary does not list or suggest all possible combinations of such features.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the specific embodiments that follow.

BRIEF DESCRIPTION OF THE DRAWINGS

FIG. 1 and SEQ ID NO:1 shows the CDS sequence of full length At5g56860.

FIG. 2 and SEQ ID NO:2 shows the amino acid sequence of At5g56860.

FIG. 3 and SEQ ID NO:3 shows the nucleic acid sequence of the rice orthologue of At5g56860.

DEFINITIONS

Figure 4:
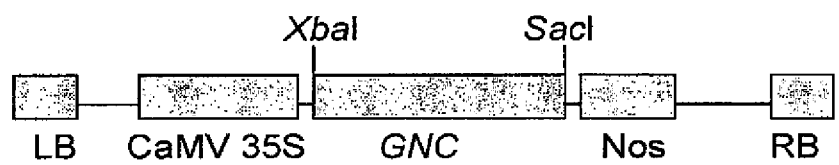
FIG. 4 is a construct of the plasmid containing CaMV 35S promoter, GNC cDNA and the nopaline synthase terminator (nos) between the right (RB) and left (LB) borders of the T-DNA.

For clarity, certain terms used in the specification are defined and presented as follows:

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric construct" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid sequence. The regulatory nucleic acid sequence of the chimeric construct is not normally operatively linked to the associated nucleic acid sequence as found in nature.

A "co-factor" is a natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

A "coding sequence" is a nucleic acid sequence that is transcribed into RNA such as mRNA, rRNA, tRNA, snRNA, sense RNA or antisense RNA. Specifically the RNA is then translated in an organism to produce a protein.

Complementary: "complementary" refers to two nucleotide sequences that comprise antiparallel nucleotide sequences capable of pairing with one another upon formation of hydrogen bonds between the complementary base residues in the antiparallel nucleotide sequences.

Enzyme activity: means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Expression Cassette: "Expression cassette" as used herein means a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or anti-sense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue or organ or stage of development.

The term "functional fragment" as used herein in relation to a nucleic acid or protein sequence means a fragment or portion of the sequence that retains the function of the full length sequence.

Gene: the term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Heterologous/exogenous: The terms "heterologous" and "exogenous" when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA) sequence naturally associated with a host cell into which it is introduced.

Hybridization: The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Inhibitor: a chemical substance that inactivates the enzymatic activity of a protein such as a biosynthetic enzyme, receptor, signal transduction protein, structural gene product, or transport protein. The term "herbicide" (or "herbicidal compound") is used herein to define an inhibitor applied to a plant at any stage of development, whereby the herbicide inhibits the growth of the plant or kills the plant.

Interaction: quality or state of mutual action such that the effectiveness or toxicity of one protein or compound on another protein is inhibitory (antagonists) or enhancing (agonists).

A nucleic acid sequence is "isocoding with" a reference nucleic acid sequence when the nucleic acid sequence encodes a polypeptide having the same amino acid sequence as the polypeptide encoded by the reference nucleic acid sequence.

Isogenic: plants that are genetically identical, except that they may differ by the presence or absence of a heterologous DNA sequence.

Isolated: in the context of the present invention, an isolated DNA molecule or an isolated enzyme is a DNA molecule or enzyme that, by human intervention, exists apart from its native environment and is therefore not a product of nature. An isolated DNA molecule or enzyme may exist in a purified form or may exist in a non-native environment such as, for example, in a transgenic host cell.

Mature protein: protein from which the transit peptide, signal peptide, and/or propeptide portions have been removed.

Minimal Promoter: the smallest piece of a promoter, such as a TATA element, that can support any transcription. A minimal promoter typically has greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Native: refers to a gene that is present in the genome of an untransformed plant cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985), Rossolini et al., Mol. Cell. Probes 8: 91-98 (1994)). The terms "nucleic acid" or "nucleic acid sequence" may also be used interchangeably with gene, cDNA, and mRNA encoded by a gene.

"ORF" means open reading frame.

Percent identity: the phrases "percent identityl" or "percent identical," in the context of two nucleic acid or protein sequences, refers to two or more sequences or subsequences that have for example 60%, specifically 70%, more specifically 80%, still more specifically 90%, even more specifically 95%, and most specifically at least 99% nucleotide or amino acid residue identity, when compared and aligned for maximum correspondence, as measured using one of the following sequence comparison algorithms or by visual inspection. Specifically, the percent identity exists over a region of the sequences that is at least about 50 residues in length, more specifically over a region of at least about 100 residues, and most specifically the percent identity exists over at least about 150 residues. In an especially specific embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequencers) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating search to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below cue to the accumulation of one or more negative-scoring residue alignments, or the end of either sequence is reached. The BLAST algorithm parameters W, T, and X determine the sensitivity and speed of the alignment. The BLASTN program (for nucleotide sequences) uses a defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity; the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more specifically less than about 0.01, and most specifically less than about 0.001.

Pre-protein: protein that is normally targeted to a cellular organelle, such as a chloroplast, and still comprises its native transit peptide.

Purified: the term "purified," when applied to a nucleic acid or protein, denotes that the nucleic acid or protein is essentially free of other cellular components with which it is associated in the natural state. It is specifically in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least about 50% pure, more specifically at least about 85% pure, and most specifically at least about 99% pure.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

"Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

Significant Increase: an increase in enzymatic activity that is larger than the margin of error inherent in the measurement technique, specifically an increase by about 2-fold or greater of the activity of the wild-type enzyme in the presence of the inhibitor, more specifically an increase by about 5-fold or greater, and most specifically an increase by about 10-fold or greater.

Significantly less: means that the amount of a product of an enzymatic reaction is reduced by more than the margin of error inherent in the measurement technique, specifically a decrease by about 2-fold or greater of the activity of the wild-type enzyme in the absence of the inhibitor, more specifically an decrease by about 5-fold or greater, and most specifically an decrease by about 10-fold or greater.

Specific Binding/immunological Cross-Reactivity: An indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions. The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) Antibodies, A Laboratory Manual, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point (Tm) for the specific sequence at a defined ionic strength and pH. Typically, under "stringent conditions" a probe will hybridize to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence specifically hybridizes to the reference nucleotide sequence in 7% sodium dodecyl sulfate (SDS), 0.5 M NaPO4, 1 mM EDTA at 50° C. with washing in 2×SSC, 0.1% SDS at 50° C., more desirably in 7% sodium dodecyl sulfate (SDS), 0.5 M NaPO4, 1 mM EDTA at 50° C. with washing in 1×SSC, 0.1% SDS at 50° C., more desirably still in 7% sodium dodecyl sulfate (SDS), 0.5 M NaPO4, 1 mM EDTA at 50° C. with washing in 0.5×SC, 0.1% SDS at 50° C., specifically in 7% sodium dodecyl sulfate (SDS), 0.5 M NaPO4, 1 mM EDTA at 50° C. with washing in 0.1×SSC, 0.1% SDS at 50° C., more specifically in 7% sodium dodecyl sulfate (SDS), 0.5 M NaPO4, 1 mM EDTA at 50° C. with washing in 0.1×SSC, 0.1% SOS at 65° C.

A "subsequence" refers to a sequence of nucleic acids or amino acids that comprise a part of a longer sequence of nucleic acids or amino acids (e.g., protein) respectively.

Substantial similarity: The term "substantial similarity" in the context of two nucleic acid or protein sequences, refers to two or more sequences or subsequences that are substantially similar, for example that have 50%, specifically 60%, more specifically 70%, even more specifically 80%, still more specifically 90%, further more specifically 95%, and most specifically 99% sequence identity.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Transformation: a process for introducing heterologous DNA into a plant cell, plant tissue, or plant. Transformed plant cells, plant tissue, or plants are understood to encompass not only the end product of a transformation process, but also transgenic progeny thereof.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

Viability: "viability" as used herein refers to a fitness parameter of a plant. Plants are assayed for their homozygous performance of plant development, indicating which proteins are essential for plant growth.

DETAILED DESCRIPTION OF THE INVENTION

I. General Description of Trait Functional Genomics

The goal of functional genomics is to identify genes controlling expression of organismal phenotypes, and employs a variety of methodologies, including but not limited to bioinformatics, gene expression studies, gene and gene product interactions, genetics, biochemistry and molecular genetics. For example, bioinformatics can assign function to a given gene by identifying genes in heterologous organisms with a high degree of similarity (homology) at the amino acid or nucleotide level. Expression of a gene at the mRNA or protein levels can assign function by linking expression of a gene to an environmental response, a developmental process or a genetic (mutational) or molecular genetic (gene overexpression or underexpression) perturbation. Expression of a gene at the mRNA level can be ascertained either alone (Northern analysis) or in concert with other genes (microarray analysis), whereas expression of a gene at the protein level can be ascertained either alone (native or denatured protein gel or immunoblot analysis) or in concert with other genes (proteomic analysis). Knowledge of protein/protein and protein/DNA interactions can assign function by identifying proteins and nucleic acid sequences acting together in the same biological process. Genetics can assign function to a gene by demonstrating that DNA lesions (mutations) in the gene have a quantifiable effect on the organism, including but not limited to: its development; hormone biosynthesis and response; growth and growth habit (plant architecture); mRNA expression profiles; protein expression profiles; ability to resist diseases; tolerance of abiotic stresses; ability to acquire nutrients; photosynthetic efficiency; altered primary and secondary metabolism; and the composition of various plant organs. Biochemistry can assign function by demonstrating that the protein encoded by the gene, typically when expressed in a heterologous organism, possesses a certain enzymatic activity, alone or in combination with other proteins. Molecular genetics can assign function by overexpressing or underexpressing the gene in the native plant or in heterologous organisms, and observing quantifiable effects as described in functional assignment by genetics above. In functional genomics, any or all of these approaches are utilized, often in concert, to assign genes to functions across any of a number of organismal phenotypes.

It is recognized by those skilled in the art that these different methodologies can each provide data as evidence for the function of a particular gene, and that such evidence is stronger with increasing amounts of data used for functional assignment: specifically from a single methodology, more specifically from two methodologies, and even more specifically from more than two methodologies. In addition, those skilled in the art are aware that different methodologies can differ in the strength of the evidence for the assignment of gene function. Typically, but not always, a datum of biochemical, genetic and molecular genetic evidence is considered stronger than a datum of bioinformatic or gene expression evidence. Finally, those skilled in the art recognize that, for different genes, a single datum from a single methodology can differ in terms of the strength of the evidence provided by each distinct datum for the assignment of the function of these different genes.

The objective of crop trait functional genomics is to identify crop trait genes, i.e. genes capable of conferring useful agronomic traits in crop plants. Such agronomic traits include, but are not limited to: enhanced yield, whether in quantity or quality; enhanced nutrient acquisition and enhanced metabolic efficiency; enhanced or altered nutrient composition of plant tissues used for food, feed, fiber or processing; enhanced utility for agricultural or industrial processing; enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. The deployment of such identified trait genes by either transgenic or non-transgenic means could materially improve crop plants for the benefit of agriculture.

Cereals are the most important crop plants on the planet, in terms of both human and animal consumption. Genomic synteny (conservation of gene order within large chromosomal segments) is observed in rice, maize, wheat, barley, rye, oats and other agriculturally important monocots, which facilitates the mapping and isolation of orthologous genes from diverse cereal species based on the sequence of a single cereal gene. Rice has the smallest (~420 Mb) genome among the cereal grains, and has recently been a major focus of public and private genomic and EST sequencing efforts.

To identify crop trait genes in the rice [wheat] genome controlling [trait], genes from the rice draft genome sequence [wheat EST databases] were prioritized based on one or more functional genomic methodologies. For example, genome-wide expression studies of rice plants infected with rice blast fungus (*Magnaporthe grisea*) were used to prioritize candidate genes controlling disease resistance. Full-length and partial cDNAs of rice trait gene candidates could then be predicted based on analysis of the rice whole-genome sequence, and isolated by designing and using primers for PCR amplification using a commercially available PCR primer-picking program. Primers were used for PCR amplification of full-length or partial cDNAs from rice cDNA libraries or first-strand cDNA. cDNA clones resulting from either approach were used for the construction of vectors designed for altering expression of these genes in transgenic plants using plant molecular genetic methodologies, which are described in detail below. Alteration of plant phenotype through overexpression or underexpression of key trait genes in transgenic plants is a robust and established method for assigning functions to plant genes. Assays to identify transgenic plants with alterations in traits of interest are to be used to unambiguously assign the utility of these genes for the improvement of rice, and by extension, other cereals, either by transgenic or classical breeding methods.

II. Identifying, Cloning and Sequencing cDNAs

The cloning and sequencing of the cDNAs of the present invention are described in Example 1.

The isolated nucleic acids and proteins of the present invention are usable over a range of plants, monocots and dicots, in particular monocots such as rice, wheat, barley and maize. In a more specific embodiment, the monocot is a cereal. In a more specific embodiment, the cereal may be, for example, maize, wheat, barley, oats, rye, millet, sorghum, triticale, secale, einkorn, spelt, emmer, teff, milo, flax, gramma grass, *Tripsacum* sp., or teosinte. In a most specific embodiment, the cereal is rice. Other plants genera include, but are not limited to, *Cucurbita, Rosa, Vitis, Juglans, Gragaria, Lotus, Medicago, Onobrychis, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*.

The present invention also provides a method of genotyping a plant or plant part comprising a nucleic acid molecule of the present invention. Optionally, the plant is a monocot such as, but not limited rice or wheat. Genotyping provides a means of distinguishing homologs of a chromosome pari and can be used to differentiate segregants in a plant population. Molecular marker methods can be used in phylogenetic studies, characterizing genetic relationships among crop varieties, identifying crosses or somatic hybrids, localizing chromosomeal segments affecting mongenic traits, map based cloning, and the study of quantitative inheritance (see Plant Molecular Biology: A Laboratory Manual, Chapter 7, Clark ed., Springer-Verlag, Berlin 1997; Paterson, A. H., "The DNA Revolution", chapter 2 in Genome Mapping in Plants, Paterson, A. H. ed., Academic Press/R.G. Lands Co., Austin, Tex. 1996).

The method of genotyping may employ any number of molecular marker analytical techniques such as, but not limited to, restriction length polymorphisms (RFLPs). As is well known in the art, RFLPs are produced by differences in the DNA restriction fragment lengths resulting from nucleotide differences between alleles of the same gene. Thus, the present invention provides a method of following segregation of a gene or nucleic acid of the present invention or chromosomal sequences genetically linked by using RFLP analysis. Linked chromosomal sequences are within 50 centiMorgans (50 cM), within 40 or 30 cM, specifically within 20 or 10 cM, more specifically within 5, 3, 2, or 1 cM of the nucleic acid of the invention.

III. Traits of Interest

The present invention encompasses the identification and isolation of polynucleotides encoding proteins involved in sugar sensing and, ultimately, in nitrogen uptake and carbon metabolism. Altering the expression of genes related to these traits can be used to improve or modify plants and/or grain, as desired. Examples describe the isolated genes of interest and methods of analyzing the alteration of expression and their effects on the plant characteristics.

One aspect of the present invention provides compositions and methods for altering (i.e. increasing or decreasing) the level of nucleic acid molecules and polypeptides of the present invention in plants. In particular, the nucleic acid molecules and polypeptides of the invention are expressed constitutively, temporally or spatially, e.g. at developmental stages, in certain tissues, and/or quantities, which are uncharacteristic of non-recombinantly engineered plants. Therefore, the present invention provides utility in such exemplary applications as altering the specified characteristics identified above.

VI. Controlling Gene Expression in Transgenic Plants

The invention further relates to transformed cells comprising the nucleic acid molecules, transformed plants, seeds, and plant parts, and methods of modifying phenotypic traits of interest by altering the expression of the genes of the invention.

A. Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence specifically includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators that operate within plant cells. This includes promoters and transcription terminators that may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (Science 261: 754-756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Specifically, as little adjacent microbial sequence as possible should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

1. Codon Usage.

The specific codon usage in plants differs from the specific codon usage in certain microorganisms. Comparison of the usage of codons within a cloned microbial ORF to usage in plant genes (and in particular genes from the target plant) will enable an identification of the codons within the ORF that should specifically be changed. Typically plant evolution has tended towards a strong preference of the nucleotides C and G in the third base position of monocotyledons, whereas dicotyledons often use the nucleotides A or T at this position. By modifying a gene to incorporate specific codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome-binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (N.A.R. 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Specific sequences adjacent to the initiating methionine may differ between different plant species. A survey of 14 maize genes located in the GenBank database provided the following results:

Position Before the Initiating ATG in 14 Maize Genes:

|   | −10 | −9 | −8 | −7 | −6 | −5 | −4 | −3 | −2 | −1 |
|---|---|---|---|---|---|---|---|---|---|---|
| C | 3 | 8 | 4 | 6 | 2 | 5 | 6 | 0 | 10 | 7 |
| T | 3 | 0 | 3 | 4 | 3 | 2 | 1 | 1 | 1 | 0 |

-continued

|   | -10 | -9 | -8 | -7 | -6 | -5 | -4 | -3 | -2 | -1 |
|---|---|---|---|---|---|---|---|---|---|---|
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the specific nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

B. Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87-94 (1991); maize—Christensen et al. Plant Molec. Biol. 12: 619-632 (1989); and *Arabidopsis*—Callis et al., J. Biol. Chem. 265:12486-12493 (1990) and Norris et al., Plant Mol. Biol. 21:895-906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491-495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice Act1 gene has been cloned and characterized (McElroy et al., Plant Cell 2: 163-171 (1990)). A 1.3 kb fragment of the promoter was found to contain all the regulatory elements required for expression in rice protoplasts. Furthermore, numerous expression vectors based on the Act1 promoter have been constructed specifically for use in monocotyledons (McElroy et al. Mol. Gen. Genet. 231: 150-160 (1991)). These incorporate the Act1-intron 1, Adh1 5' flanking sequence and Adh1-intron 1 (from the maize alcohol dehydrogenase gene) and sequence from the CaMV 35S promoter. Vectors showing highest expression were fusions of 35S and Act1 intron or the Act1 5' flanking sequence and the Act1 intron. Optimization of sequences around the initiating ATG (of the GUS reporter gene) also enhanced expression. The promoter expression cassettes described by McElroy et al. (Mol. Gen. Genet. 231: 150-160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice Actl promoter with its first intron has also been found to direct high expression in cultured barley cells (Chibbar et al. Plant Cell Rep. 12: 506-509 (1993)).

d. Inducible Expression, PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the *Arabidopsis* PR-1 promoter described in Lebel et al., Plant J. 16:223-233 (1998) may be used. The promoter of choice is specifically excised from its source by restriction enzymes, but can alternatively be PCR-amplified using primers that carry appropriate terminal restriction sites. Should PCR-amplification be undertaken, the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., Plant Cell 4: 645-656 (1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is accomplished by cleavage with XhoI and blunting with T4 polymerase, followed by cleavage with HindIII, and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) Nat. Biotechnol 16:177-180). In *A. nidulans*, the alcA gene encodes alcohol dehydrogenase 1, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) Nat. Biotechnol 16:177-180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) The Plant Journal 11: 605-612) and gene expression is induced by application of a glucocorticoid, for example a synthetic glucocorticoid, specifically dexamethasone, specifically at a concentration ranging from 0.1 mM to 1 mM, more specifically from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) Science 231: 699-704) fused to the transactivating domain of the herpes viral protein VP16 (Triezenberg et al. (1988) Genes Devel. 2: 718-729) fused to the hormone-binding domain of the rat glucocorticoid receptor (Picard et al. (1988) Cell 54: 1073-1080). The expression of the fusion protein is controlled either by a promoter known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is the promoter of the maize metallothionein-like (MTL) gene described by de Framond (FEBS 290: 103-106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)) and all are suitable for use with the instant invention. Logemann et al. describe the 5' upstream sequences of the dicotyledonous potato wun1 gene. Xu et al. show that a wound-inducible promoter from the dicotyledon potato (pin2) is active in the monocotyledon rice. Further, Rohrmeier & Lehle describe the cloning of the maize Wip1 cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Specific Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof can be transferred to a vector such as pCGN1761 where it can replace the 35S promoter and be used to drive the expression of a foreign gene in a pith-specific manner. In fact, fragments containing the pith-specific promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15; 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology. 84:965-968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., Plant Cell 3: 317 (1991). The derived Bz1 core promoter fragment thus extends from −53 to +227 and includes the Bz1 intron-1 in the 5' untranslated region. Also useful for the invention is a minimal promoter created by use of a synthetic TATA element, The TATA element allows recognition of the promoter by RNA polymerase factors and confers a basal level of gene expression in the absence of activation (see generally, Mukumoto (1993) Plant Mol Biol 23; 995-1003; Green (2000) Trends Biochem Sci 25: 59-63)

4. Targeting of the Gene Product within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411-418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512-6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081-1091 (1982) and Wasmann et al. Mol. Gen. Genet. 205: 446-453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

C. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the specific transformation technique and the target species for transformation. For certain target species, different antibiotic or herbicide selection markers may be specific. Selection markers used routinely in transformation include the nptII gene, which confers resistance to kanamycin and related antibiotics (Messing & Vierra. Gene 19; 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994, 629).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

a. pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446-455 (1985)) allowing excision of the tetracycline-resistance gene, followed by insertion of an AccI fragment from pUC4K carrying an NPTII (Messing & Vierra, Gene 19: 259-268 (1982): Bevan et al., Nature 304: 184-187 (1983): McBride et al., Plant Molecular Biology 14: 266-276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153-161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives Thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153-161 (1987)). Various derivatives of pCIB10 are constructed which incorporate the gene for hygromycin B phosphotransferase described by Gritz et al. (Gene 25: 179-188 (1983)). These derivatives enable selection of transgenic plant cells on hygromycin only (pCIB743), or hygromycin and kanamycin (pCIB715, pCIB717).

2. Vectors Suitable for Non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the specific selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces* viridochromogenes is excised and inserted into the HpaI site of pCIB3060 (Thompson et al. EMBO J 6: 2519-2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

D Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include *Agrobacterium*-based techniques and techniques that do not require *Agrobacterium*. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a specific technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Specific techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus. A specific technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference. For this example, rice (*Oryza sativa*) is used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 mil/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for ~2 days at 28° C. *Agrobacterium* is re-suspended in liquid MS-CIM medium. The *Agrobacterium* culture is diluted to an OD600 of 0.2-0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcilin (400 mg/liter) to inhibit the growth of *Agrobacterium*. For constructs utilizing the PMI selectable marker gene (Reed et al., In Vitro Cell. Dev. Biol.-Plant 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (TO generation) grown to maturity, and the T1 seed is harvested.

3. Transformation of Plastids

Seeds of *Nicotiana tabacum* c.v. 'Xanthi nc' are germinated seven per plate in a 1" circular array on T agar medium and bombarded 12-14 days after sowing with 1 µm tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 µmol photons/m2/s) on plates of RMOP medium (Svab, Z., Hajdukiewicz, P. and Maliga, P. (1990) PNAS 87, 8526-8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346-349) is separated on 1% Tris-borate (TBE) agarose gels, transferred to nylon membranes (Amersham) and probed with 32P-labeled random primed DNA sequences corresponding to a 0.7 kb BamHI/HindIII DNA fragment from pCB containing a portion of the rps7/12 plastid targeting sequence. Homoplasmic shoots are rooted aseptically on spectinomycin-containing MS/IBA medium (McBride, K. E. et al. (1994) PNAS 91, 7301-7305) and transferred to the greenhouse.

V. Breeding and Seed Production

A. Breeding

The plants obtained via transformation with a nucleic acid sequence of the present invention can be any of a wide variety of plant species, including those of monocots and dicots; however, the plants used in the method of the invention are specifically selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

B. Seed Production

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

VI. Alteration of Expression of Nucleic Acid Molecules

The alteration in expression of the nucleic acid molecules of the present invention is achieved in one of the following ways:

A. "Sense" Suppression

Alteration of the expression of a nucleotide sequence of the present invention, specifically reduction of its expression, is obtained by "sense" suppression (referenced in e.g. Jorgensen et al. (1996) Plant Mol. Biol. 31, 957-973). In this case, the entirety or a portion of a nucleotide sequence of the present invention is comprised in a DNA molecule. The DNA molecule is specifically operatively linked to a promoter functional in a cell comprising the target gene, specifically a plant cell, and introduced into the cell, in which the nucleotide sequence is expressible. The nucleotide sequence is inserted in the DNA molecule in the "sense orientation", meaning that the coding strand of the nucleotide sequence can be transcribed. In a specific embodiment, the nucleotide sequence is fully translatable and all the genetic information comprised in the nucleotide sequence, or portion thereof, is translated into a polypeptide. In another specific embodiment, the nucleotide sequence is partially translatable and a short peptide is translated. In a specific embodiment, this is achieved by inserting at least one premature stop codon in the nucleotide sequence, which bring translation to a halt. In another more specific embodiment, the nucleotide sequence is transcribed but no translation product is being made. This is usually achieved by removing the start codon, e.g. the "ATG", of the polypeptide encoded by the nucleotide sequence. In a further specific embodiment, the DNA molecule comprising the nucleotide sequence, or a portion thereof, is stably integrated in the genome of the plant cell. In another specific embodiment, the DNA molecule comprising the nucleotide sequence, or a portion thereof, is comprised in an extrachromosomally replicating molecule.

In transgenic plants containing one of the DNA molecules described immediately above, the expression of the nucleotide sequence corresponding to the nucleotide sequence comprised in the DNA molecule is specifically reduced. Specifically, the nucleotide sequence in the DNA molecule is at least 70% identical to the nucleotide sequence the expression of which is reduced, more specifically it is at least 80% identical, yet more specifically at least 90% identical, yet more specifically at least 95% identical, yet more specifically at least 99% identical B. "Anti-Sense" Suppression In another specific embodiment, the alteration of the expression of a nucleotide sequence of the present invention, specifically the reduction of its expression is obtained by "anti-sense" suppression. The entirety or a portion of a nucleotide sequence of the present invention is comprised in a DNA molecule. The DNA molecule is specifically operatively linked to a promoter functional in a plant cell, and introduced in a plant cell, in which the nucleotide sequence is expressible. The nucleotide sequence is inserted in the DNA molecule in the "anti-sense orientation", meaning that the reverse complement (also called sometimes non-coding strand) of the nucleotide sequence can be transcribed. In a specific embodiment, the DNA molecule comprising the nucleotide sequence, or a portion thereof, is stably integrated in the genome of the plant cell. In another specific embodiment the DNA molecule comprising the nucleotide sequence, or a portion thereof, is comprised in an extrachromosomally replicating molecule. Several publications describing this approach are cited for further illustration (Green, P. J. et al., Ann. Rev. Biochem. 55:569-597 (1986); van der Krol, A. R. et al, Antisense Nuc. Acids & Proteins, pp. 125-141 (1991); Abel, P. P. et al., PNASroc. Natl. Acad. Sci. USA 86:6949-6952 (1989); Ecker, J. R. et al., Proc. Natl. Acad. Sci. USANAS 83:5372-5376 (August 1986)).

In transgenic plants containing one of the DNA molecules described immediately above, the expression of the nucleotide sequence corresponding to the nucleotide sequence comprised in the DNA molecule is specifically reduced. Specifically, the nucleotide sequence in the DNA molecule is at least 70% identical to the nucleotide sequence the expression of which is reduced, more specifically it is at least 80% identical, yet more specifically at least 90% identical, yet more specifically at least 95% identical, yet more specifically at least 99% identical.

C. Homologous Recombination

In another specific embodiment, at least one genomic copy corresponding to a nucleotide sequence of the present invention is modified in the genome of the plant by homologous recombination as further illustrated in Paszkowski et al., EMBO Journal 7:4021-26 (1988). This technique uses the property of homologous sequences to recognize each other and to exchange nucleotide sequences between each by a process known in the art as homologous recombination. Homologous recombination can occur between the chromosomal copy of a nucleotide sequence in a cell and an incoming copy of the nucleotide sequence introduced in the cell by transformation. Specific modifications are thus accurately introduced in the chromosomal copy of the nucleotide sequence. In one embodiment, the regulatory elements of the nucleotide sequence of the present invention are modified. Such regulatory elements are easily obtainable by screening a genomic library using the nucleotide sequence of the present invention, or a portion thereof, as a probe. The existing regulatory elements are replaced by different regulatory elements, thus altering expression of the nucleotide sequence, or they are mutated or deleted, thus abolishing the expression of the nucleotide sequence. In another embodiment, the nucleotide sequence is modified by deletion of a part of the nucleotide sequence or the entire nucleotide sequence, or by mutation. Expression of a mutated polypeptide in a plant cell is also contemplated in the present invention. More recent refinements of this technique to disrupt endogenous plant genes have been described (Kempin et al., Nature 389:802-803 (1997) and Miao and Lam, Plant J., 7:359-365 (1995).

In another specific embodiment, a mutation in the chromosomal copy of a nucleotide sequence is introduced by transforming a cell with a chimeric oligonucleotide composed of a contiguous stretch of RNA and DNA residues in a duplex conformation with double hairpin caps on the ends. An additional feature of the oligonucleotide is for example the presence of 2'-O-methylation at the RNA residues. The RNA/DNA sequence is designed to align with the sequence of a chromosomal copy of a nucleotide sequence of the present invention and to contain the desired nucleotide change. For example, this technique is further illustrated in U.S. Pat. No. 5,501,967 and Zhu et al. (1999) Proc. Natl. Acad. Sci. USA 96: 8768-8773.

D. Ribozymes

In a further embodiment, the RNA coding for a polypeptide of the present invention is cleaved by a catalytic RNA, or ribozyme, specific for such RNA. The ribozyme is expressed in transgenic plants and results in reduced amounts of RNA coding for the polypeptide of the present invention in plant cells, thus leading to reduced amounts of polypeptide accumulated in the cells. This method is further illustrated in U.S. Pat. No. 4,987,071.

E. Dominant-Negative Mutants

In another specific embodiment, the activity of the polypeptide encoded by the nucleotide sequences of this invention is changed. This is achieved by expression of dominant negative mutants of the proteins in transgenic plants, leading to the loss of activity of the endogenous protein.

F. Aptamers

In a further embodiment, the activity of polypeptide of the present invention is inhibited by expressing in transgenic plants nucleic acid ligands, so-called aptamers, which specifically bind to the protein. Aptamers are preferentially obtained by the SELEX (Systematic Evolution of Ligands by Exponential Enrichment) method. In the SELEX method, a candidate mixture of single stranded nucleic acids having regions of randomized sequence is contacted with the protein and those nucleic acids having an increased affinity to the target are partitioned from the remainder of the candidate mixture. The partitioned nucleic acids are amplified to yield a ligand enriched mixture. After several iterations a nucleic acid with optimal affinity to the polypeptide is obtained and is used for expression in transgenic plants. This method is further illustrated in U.S. Pat. No. 5,270,163.

G. Zinc Finger Proteins

A zinc finger protein that binds a nucleotide sequence of the present invention or to its regulatory region is also used to alter expression of the nucleotide sequence. Specifically, transcription of the nucleotide sequence is reduced or increased. Zinc finger proteins are for example described in Beerli et al. (1998) PNAS 95:14628-14633., or in WO 95/19431, WO 98/54311, or WO 96/06166, all incorporated herein by reference in their entirety.

H. dsRNA

Alteration of the expression of a nucleotide sequence of the present invention is also obtained by dsRNA interference as described for example in WO 99/32619, WO 99/53050 or WO 99/61631, all incorporated herein by reference in their entirety. In another specific embodiment, the alteration of the expression of a nucleotide sequence of the present invention, specifically the reduction of its expression, is obtained by double-stranded RNA (dsRNA) interference. The entirety or, specifically a portion of a nucleotide sequence of the present invention is comprised in a DNA molecule. The size of the DNA molecule is specifically from 100 to 1000 nucleotides or more; the optimal size to be determined empirically. Two copies of the identical DNA molecule are linked, separated by a spacer DNA molecule, such that the first and second copies are in opposite orientations. In the specific embodiment, the first copy of the DNA molecule is in the reverse complement (also known as the non-coding strand) and the second copy is the coding strand; in the most specific embodiment, the first copy is the coding strand, and the second copy is the reverse complement. The size of the spacer DNA molecule is specifically 200 to 10,000 nucleotides, more specifically 400 to 5000 nucleotides and most specifically 600 to 1500 nucleotides in length. The spacer is specifically a random piece of DNA, more specifically a random piece of DNA without homology to the target organism for dsRNA interference, and most specifically a functional intron which is effectively spliced by the target organism. The two copies of the DNA molecule separated by the spacer are operatively linked to a promoter functional in a plant cell, and introduced in a plant cell, in which the nucleotide sequence is expressible. In a specific embodiment, the DNA molecule comprising the nucleotide sequence, or a portion thereof, is stably integrated in the genome of the plant cell. In another specific embodiment the DNA molecule comprising the nucleotide sequence, or a portion thereof, is comprised in an extrachromosomally replicating molecule. Several publications describing this approach are cited for further illustration (Waterhouse et al. (1998) PNAS 95:13959-13964; Chuang and Meyerowitz (2000) PNAS 97:4985-4990; Smith et al. (2000) Nature 407: 319-320). Alteration of the expression of a nucleotide sequence by dsRNA interference is also described in, for example WO 99/32619, WO 99/53050 or WO 99/61631, all incorporated herein by reference in their entirety.

In transgenic plants containing one of the DNA molecules described immediately above, the expression of the nucleotide sequence corresponding to the nucleotide sequence comprised in the DNA molecule is specifically reduced. Specifically, the nucleotide sequence in the DNA molecule is at least 70% identical to the nucleotide sequence the expression of which is reduced, more specifically it is at least 80% identical, yet more specifically at least 90% identical, yet more specifically at least 95% identical, yet more specifically at least 99% identical.

I. Insertion of a DNA Molecule (Insertional Mutagenesis)

In another specific embodiment, a DNA molecule is inserted into a chromosomal copy of a nucleotide sequence of the present invention, or into a regulatory region thereof. Specifically, such DNA molecule comprises a transposable element capable of transposition in a plant cell, such as e.g. Ac/Ds, Em/Spm, mutator. Alternatively, the DNA molecule comprises a T-DNA border of an *Agrobacterium* T-DNA. The DNA molecule may also comprise a recombinase or integrase recognition site which can be used to remove part of the DNA molecule from the chromosome of the plant cell. Methods of insertional mutagenesis using T-DNA, transposons, oligonucleotides or other methods known to those skilled in the art are also encompassed. Methods of using T-DNA and transposon for insertional mutagenesis are described in Winkler et al. (1989) Methods Mol. Biol. 82:129-136 and Martienssen (1998) PNAS 95:2021-2026, incorporated herein by reference in their entireties.

J. Deletion Mutagenesis

In yet another embodiment, a mutation of a nucleic acid molecule of the present invention is created in the genomic copy of the sequence in the cell or plant by deletion of a portion of the nucleotide sequence or regulator sequence. Methods of deletion mutagenesis are known to those skilled in the art. See, for example, Miao et al., (1995) Plant J. 7:359.

In yet another embodiment, this deletion is created at random in a large population of plants by chemical mutagenesis or irradiation and a plant with a deletion in a gene of the present invention is isolated by forward or reverse genetics. Irradiation with fast neutrons or gamma rays is known to cause deletion mutations in plants (Silverstone et al, (1998) Plant Cell, 10:155-169; Bruggemann et al., (1996) Plant J., 10:755-760; Redei and Koncz in Methods in *Arabidopsis* Research, World Scientific Press (1992), pp. 16-82). Deletion mutations in a gene of the present invention can be recovered in a reverse genetics strategy using PCR with pooled sets of genomic DNAs as has been shown in *C. elegans* (Liu et al., (1999), Genome Research, 9:859-867.). A forward genetics strategy would involve mutagenesis of a line displaying PTGS followed by screening the M2 progeny for the absence of PTGS. Among these mutants would be expected to be some that disrupt a gene of the present invention. This could be assessed by Southern blot or PCR for a gene of the present invention with genomic DNA from these mutants.

K. Overexpression in a Plant Cell

In yet another specific embodiment, a nucleotide sequence of the present invention encoding a polypeptide is over-expressed. Examples of nucleic acid molecules and expression cassettes for over-expression of a nucleic acid molecule of the present invention are described above. Methods known to those skilled in the art of over-expression of nucleic acid molecules are also encompassed by the present invention.

In a specific embodiment, the expression of the nucleotide sequence of the present invention is altered in every cell of a plant. This is for example obtained though homologous recombination or by insertion in the chromosome. This is also for example obtained by expressing a sense or antisense RNA, zinc finger protein or ribozyme under the control of a promoter capable of expressing the sense or antisense RNA, zinc finger protein or ribozyme in every cell of a plant. Constitutive expression, inducible, tissue-specific or developmentally-regulated expression are also within the scope of the present invention and result in a constitutive, inducible, tissue-specific or developmentally-regulated alteration of the expression of a nucleotide sequence of the present invention in the plant cell. Constructs for expression of the sense or antisense RNA, zinc finger protein or ribozyme, or for overexpression of a nucleotide sequence of the present invention, are prepared and transformed into a plant cell according to the teachings of the present invention, e.g. as described infra.

VII. Polypeptides

The present invention further relates to isolated polypeptides comprising the amino acid sequence of SEQ ID NO:2. In particular, isolated polypeptides comprising the amino acid sequence of SEQ ID NO:2, and variants having conservative amino acid modifications. One skilled in the art will recognize that individual substitutions, deletions or additions to a nucleic acid, peptide, polypeptide or protein sequence which alters, adds or deletes a single amino acid or a small percent of amino acids in the encoded sequence is a "conservative modification" where the modification results in the substitution of an amino acid with a chemically similar amino acid. Conservative modified variants provide similar biological activity as the unmodified polypeptide. Conservative substitution tables listing functionally similar amino acids are known in the art. See Crighton (1984) Proteins, W.H. Freeman and Company.

In a specific embodiment, a polypeptide having substantial similarity to a polypeptide sequence of SEQ ID NO:2, or exon or domain thereof, is an allelic variant of the polypeptide sequence listed in SEQ ID NO:2. In another specific embodiment, a polypeptide having substantial similarity to a polypeptide sequence listed in SEQ ID NO:2, or exon or domain thereof, is a naturally occurring variant of the polypeptide sequence listed SEQ ID NO:2. In another specific embodiment, a polypeptide having substantial similarity to a polypeptide sequence listed SEQ ID NO:2, or exon or domain thereof, is a polymorphic variant of the polypeptide sequence listed in SEQ ID NO:2.

In an alternate specific embodiment, the sequence having substantial similarity contains a deletion or insertion of at least one amino acid. In a more specific embodiment, the deletion or insertion is of less than about ten amino acids. In a most specific embodiment, the deletion or insertion is of less than about three amino acids.

In a specific embodiment, the sequence having substantial similarity encodes a substitution in at least one amino acid.

Embodiments of the present invention also contemplate an isolated polypeptide containing a polypeptide sequence including (a) a polypeptide sequence listed in SEQ ID NO:2, or exon or domain thereof;

(b) a polypeptide sequence having substantial similarity to (a);

(c) a polypeptide sequence encoded by a nucleotide sequence identical to or having substantial similarity to a nucleotide sequence listed in SEQ ID NO:1, or an exon or domain thereof, or a sequence complementary thereto;

(d) a polypeptide sequence encoded by a nucleotide sequence capable of hybridizing under medium stringency conditions to a nucleotide sequence listed in SEQ ID NO:1, or to a sequence complementary thereto; or (e) a functional fragment of (a), (b), (c) or (d).

In another specific embodiment, the polypeptide having substantial similarity is an allelic variant of a polypeptide sequence listed in SEQ ID NO:2, or a fragment, domain, repeat or chimeras thereof. In another specific embodiment, the isolated nucleic acid includes a plurality of regions from the polypeptide sequence encoded by a nucleotide sequence identical to or having substantial similarity to a nucleotide sequence listed in SEQ ID NO:1, or fragment or domain thereof, or a sequence complementary thereto.

In another specific embodiment, the polypeptide is a polypeptide sequence listed in SEQ ID NO:2. In another specific embodiment, the polypeptide is a functional fragment or domain. In yet another specific embodiment, the polypeptide is a chimera, where the chimera may include functional protein domains, including domains, repeats, post-translational modification sites, or other features. In a more specific embodiment, the polypeptide is a plant polypeptide. In a more specific embodiment, the plant is a dicot. In a more specific embodiment, the plant is a gymnosperm. In a more specific embodiment, the plant is a monocot. In a more specific embodiment, the monocot is a cereal. In a more specific embodiment, the cereal may be, for example, maize, wheat, barley, oats, rye, millet, sorghum, triticale, secale, einkorn, spelt, emmer, teff, milo, flax, gramma grass, *Tripsacum*, and teosinte. In another specific embodiment, the cereal is rice.

In a specific embodiment, the polypeptide is expressed in a specific location or tissue of a plant. In a more specific embodiment, the location or tissue is for example, but not limited to, epidermis, vascular tissue, meristem, cambium, cortex or pith. In a most specific embodiment, the location or tissue is leaf or sheath, root, flower, and developing ovule or seed. In a more specific embodiment, the location or tissue may be, for example, epidermis, root, vascular tissue, meristem, cambium, cortex, pith, leaf, and flower. In a more specific embodiment, the location or tissue is a seed.

In a specific embodiment, the polypeptide sequence encoded by a nucleotide sequence having substantial similarity to a nucleotide sequence listed in SEQ ID NO:1 or a fragment or domain thereof or a sequence complementary thereto, includes a deletion or insertion of at least one nucleotide. In a more specific embodiment, the deletion or insertion is of less than about thirty nucleotides. In a most specific embodiment, the deletion or insertion is of less than about five nucleotides.

In a specific embodiment, the polypeptide sequence encoded by a nucleotide sequence having substantial similarity to a nucleotide sequence listed in SEQ ID NO:1, or fragment or domain thereof or a sequence complementary thereto, includes a substitution of at least one codon. In a more specific embodiment, the substitution is conservative.

In a specific embodiment, the polypeptide sequences having substantial similarity to the polypeptide sequence listed in SEQ ID NO:2, or a fragment, domain, repeat or chimeras thereof includes a deletion or insertion of at least one amino acid.

The polypeptides of the invention, fragments thereof or variants thereof can comprise any number of contiguous amino acid residues from a polypeptide of the invention, wherein the number of residues is selected from the group of integers consisting of from 10 to the number of residues in a full-length polypeptide of the invention. Specifically, the portion or fragment of the polypeptide is a functional protein. The present invention includes active polypeptides having specific activity of at least 20%, 30%, or 40%, and specifically at least 505, 60%, or 70%, and most specifically at least 805, 90% or 95% that of the native (non-synthetic) endogenous polypeptide. Further, the substrate specificity (kcat/Km) is optionally substantially similar to the native (non-synthetic), endogenous polypeptide. Typically the Km will be at least 30%, 40%, or 50% of the native, endogenous polypeptide; and more specifically at least 605, 70%, 80%, or 90%. Methods of assaying and quantifying measures of activity and substrate specificity are well known to those of skill in the art.

The isolated polypeptides of the present invention will elicit production of an antibody specifically reactive to a polypeptide of the present invention when presented as an immunogen. Therefore, the polypeptides of the present invention can be employed as immunogens for constructing antibodies immunoreactive to a protein of the present invention for such purposes, but not limited to, immunoassays or protein purification techniques. Immunoassays for determining binding are well known to those of skill in the art such as, but not limited to, ELISAs or competitive immunoassays.

Embodiments of the present invention also relate to chimeric polypeptides encoded by the isolated nucleic acid molecules of the present disclosure including a chimeric polypeptide containing a polypeptide sequence encoded by an isolated nucleic acid containing a nucleotide sequence including:

(a) a nucleotide sequence listed in SEQ ID NO:1, or an exon or domain thereof;

(b) a nucleotide sequence having substantial similarity to (a);

(c) a nucleotide sequence capable of hybridizing to (a);

(d) a nucleotide sequence complementary to (a), (b) or (c); and (e) a nucleotide sequence which is the reverse complement of (a), (b) or (c); or (f) a functional fragment thereof.

A polypeptide containing a polypeptide sequence encoded by an isolated nucleic acid containing a nucleotide sequence, its complement, or its reverse complement, encoding a polypeptide including a polypeptide sequence including:

(a) a polypeptide sequence listed in SEQ ID NO:2, or a domain, repeat or chimeras thereof;

(b) a polypeptide sequence having substantial similarity to (a);

(c) a polypeptide sequence encoded by a nucleotide sequence identical to or having substantial similarity to a nucleotide sequence listed in SEQ ID NO:1, or an exon or domain thereof or a sequence complementary thereto;

(d) a polypeptide sequence encoded by a nucleotide sequence capable of hybridizing under medium stringency conditions to a nucleotide sequence listed in SEQ ID NO:1, or to a sequence complementary thereto; and a functional fragment of (a), (b), (c) or (d); or (e) a functional fragment thereof.

The isolated nucleic acid molecules of the present invention are useful for expressing a polypeptide of the present invention in a recombinantly engineered cell such as a bacteria, yeast, insect, mammalian or plant cell. The cells produce the polypeptide in a non-natural condition (e.g. in quantity, composition, location and/or time) because they have been genetically altered to do so. Those skilled in the art are knowledgeable in the numerous expression systems available for expression of nucleic acids encoding a protein of the present invention, and will not be described in detail below.

Briefly, the expression of isolated nucleic acids encoding a polypeptide of the invention will typically be achieved, for example, by operably linking the nucleic acid or cDNA to a promoter (constitutive or regulatable) followed by incorporation into an expression vector. The vectors are suitable for replication and/or integration in either prokaryotes or eukaryotes. Commonly used expression vectors comprise transcription and translation terminators, initiation sequences and promoters for regulation of the expression of the nucleic acid molecule encoding the polypeptide. To obtain high levels of expression of the cloned nucleic acid molecule, it is desirable to use expression vectors comprising a strong promoter to direct transcription, a ribosome binding site for translation initiation, and a transcription/translation terminator. One skilled in the art will recognize that modifications may be made to the polypeptide of the present invention without diminishing its biological activity. Some modifications may be made to facilitate the cloning, expression or incorporation of the polypeptide of the invention into a fusion protein. Such modification are well known in the art and include, but are not limited to, a methionine added at the amino terminus to provide an initiation site, or additional amino acids (e.g. poly Histadine) placed on either terminus to create conveniently located purification sequences Restriction sites or termination codons can also be introduced into the vector.

In a specific embodiment, the expression vector includes one or more elements such as, for example, but not limited to, a promoter-enhancer sequence, a selection marker sequence, an origin of replication, an epitope-tag encoding sequence, or an affinity purification-tag encoding sequence. In a more specific embodiment, the promoter-enhancer sequence may be, for example, the CaMV 35S promoter, the CaMV 19S promoter, the tobacco PR-1a promoter, the ubiquitin promoter, and the phaseolin promoter. In another embodiment, the promoter is operable in plants, and more specifically, a constitutive or inducible promoter. In another specific embodiment, the selection marker sequence encodes an antibiotic resistance gene. In another specific embodiment, the epitope-tag sequence encodes V5, the peptide Phe-His-His-Thr-Thr, hemagglutinin, or glutathione-S-transferase. In another specific embodiment the affinity purification-tag sequence encodes a polyamino acid sequence or a polypeptide. In a more specific embodiment, the polyamino acid sequence is polyhistidine. In a more specific embodiment, the polypeptide is chitin binding domain or glutathione-S-transferase. In a more specific embodiment, the affinity purification-tag sequence comprises an intein encoding sequence.

Prokaryotic cells may be used a host cells, for example, but not limited to, *Escherichia coli*, and other microbial strains known to those in the art. Methods for expressing proteins in prokaryotic cells are well known to those in the art and can be found in many laboratory manuals such as Molecular Cloning: A Laboratory Manual, by J. Sambrook et al. (1989, Cold Spring Harbor Laboratory Press). A variety of promoters, ribosome binding sites, and operators to control expression are available to those skilled in the art, as are selectable markers such as antibiotic resistance genes. The type of vector chosen is to allow for optimal growth and expression in the selected cell type.

A variety of eukaryotic expression systems are available such as, but not limited to, yeast, insect cell lines, plant cells and mammalian cells. Expression and synthesis of heterologous proteins in yeast is well known (see Sherman et al., Methods in Yeast Genetics, Cold Spring Harbor Laboratory Press, 1982). Commonly used yeast strains widely used for production of eukaryotic proteins are *Saccharomyces cerevisiae* and *Pichia pastoris*, and vectors, strains and protocols for expression are available from commercial suppliers (e.g., Invitrogen).

Mammalian cell systems may be transfected with expression vectors for production of proteins. Many suitable host cell lines are available to those in the art, such as, but not limited to the HEK293, BHK21 and CHO cells lines. Expression vectors for these cells can include expression control sequences such as an origin of replication, a promoter, (e.g., the CMV promoter, a HSV tk promoter or phosphoglycerate kinase (pgk) promoter), an enhancer, and protein processing sites such as ribosome binding sites, RNA splice sites, polyadenylation sites, and transcription terminator sequences. Other animal cell lines useful for the production of proteins are available commercially or from depositories such as the American Type Culture Collection.

Expression vectors for expressing proteins in insect cells are usually derived from the SF9 baculovirus or other viruses known in the art. A number of suitable insect cell lines are available including but not limited to, mosquito larvae, silkworm, armyworm, moth and *Drosophila* cell lines.

Methods of transfecting animal and lower eukaryotic cells are known. Numerous methods are used to make eukaryotic cells competent to introduce DNA such as but not limited to: calcium phosphate precipitation, fusion of the recipient cell with bacterial protoplasts containing the DNA, treatment of the recipient cells with liposomes containing the DNA, DEAE dextrin, electroporation, biolistics, and microinjection of the DNA directly into the cells. Transfected cells are cultured using means well known in the art (see, Kuchler, R. J., Biochemical Methods in Cell Culture and Virology, Dowden, Hutchinson and Ross, Inc. 1997).

Once a polypeptide of the present invention is expressed it may be isolated and purified from the cells using methods known to those skilled in the art. The purification process may be monitored using Western blot techniques or radioimmunoassay or other standard immunoassay techniques. Protein purification techniques are commonly known and used by those in the art (see R. Scopes, Protein Purification: Principles and Practice, Springer-Verlag, New York 1982: Deutscher, Guide to Protein Purification, Academic Press (1990). Embodiments of the present invention provide a method of producing a recombinant protein in which the expression vector includes one or more elements including a promoter-enhancer sequence, a selection marker sequence, an origin of replication, an epitope-tag encoding sequence, and an affinity purification-tag encoding sequence. In one specific embodiment, the nucleic acid construct includes an epitope-tag encoding sequence and the isolating step includes use of an antibody specific for the epitope-tag. In another specific embodiment, the nucleic acid construct contains a polyamino acid encoding sequence and the isolating step includes use of a resin comprising a polyamino acid binding substance, specifically where the polyamino acid is polyhistidine and the polyamino binding resin is nickel-charged agarose resin. In yet another specific embodiment, the nucleic acid construct contains a polypeptide encoding sequence and the isolating step includes the use of a resin containing a polypeptide binding substance, specifically where the polypeptide is a chitin binding domain and the resin contains chitin-sepharose.

The polypeptides of the present invention can be synthesized using non-cellular synthetic methods known to those in the art. Techniques for solid phase synthesis are described by Barany and Mayfield, Solid-Phase Peptide Synthesis, pp. 3-284 in the Peptides: Analysis, Synthesis, Biology, Vol. 2, Special Methods in Peptide Synthesis, Part A; Merrifield, et al., J. Am. Chem. Soc. 85:2149-56 (1963) and Stewart et al., Solid Phase Peptide Synthesis, 2nd ed. Pierce Chem. Co., Rockford, Ill. (1984).

The present invention further provides a method for modifying (i.e. increasing or decreasing) the concentration or composition of the polypeptides of the invention in a plant or part thereof. Modification can be effected by increasing or decreasing the concentration and/or the composition (i.e. the ratio of the polypeptides of the present invention) in a plant. The method comprised introducing into a plant cell with an expression cassette comprising a nucleic acid molecule of the present invention, or an nucleic acid encoding a At5g56860 sequence as described above to obtain a transformed plant cell or tissue, culturing the transformed plant cell or tissue.

The nucleic acid molecule can be under the regulation of a constitutive or inducible promoter. The method can further comprise inducing or repressing expression of a nucleic acid molecule of a sequence in the plant for a time sufficient to modify the concentration and/or composition in the plant or plant part.

A plant or plant part having modified expression of a nucleic acid molecule of the invention can be analyzed and selected using methods known to those skilled in the art such as, but not limited to, Southern blot, DNA sequencing, or PCR analysis using primers specific to the nucleic acid molecule and detecting amplicons produced therefrom.

In general, concentration or composition in increased or decreased by at least 5%, 10%, 20%, 30%, 40%, 50%, 60%, 70%, 80% or 90% relative to a native control plant, plant part or cell lacking the expression cassette.

Sugars are central regulators of many vital processes in photosynthetic plants, such as photosynthesis, carbon and nitrogen metabolism and this regulation is achieved by regulating gene expression, either activate or repress genes involved. The mechanisms by which sugars control gene expression are not understood well. This GATA transcription factor disclosed here is involved in regulating sugar sensing and the expression of the factor itself is influenced by the change of the N status. Increased expression of this gene can produce plants with increased yield, particularly as the manipulation of sugar signaling pathways can lead to increased photosynthesis and increased nitrogen utilization and alter source-sink relationships in seeds, tubes, roots and other storage organs.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by J. Sambrook, et al., Molecular Cloning: A Laboratory Manual, 3d Ed., Cold Spring Harbor, N.Y.: Cold Spring Harbor Laboratory Press (2001); by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, New York, John Wiley and Sons Inc., (1988), Reiter, et al., Methods in *Arabidopsis* Research, World Scientific Press (1992), and Schultz et al., Plant Molecular Biology Manual, Kluwer Academic Publishers (1.998).

Experimental Background and Procedures

A. Determining Rice and Maize Growth Conditions Under Limiting Nitrogen Conditions In past experiments to study genes involved in nitrate uptake and assimilation, the present inventors and others have utilized growth conditions in which nitrate was generally either present in excess or absent in its entirety. In the latter case, nitrate is typically added to plants grown in its absence in order to understand nitrate regulation of these and other genes. While this type of extreme treatment is useful in defining some aspects of gene regulation, it is not suitable to gain a better understanding of the effect of nitrogen limitation. The inventors have defined conditions for *Arabidopsis* in which nitrogen limits growth. This involved developing a system using Rockwool (Hirai et al., 1995 Plant Cell Physiol 36, 1331-1339) and defining three conditions: one where growth is maximal; one where nitrogen limits growth to 70-75% maximal growth levels; one where there is a more severe limitation to 30-35% maximal growth levels. The nitrogen limitation acts as a 'stress' with the amount of 'stress' easily varied by altering the concentration of nitrate. The inventors assay the physiological "nitrogen status" by measuring nitrate, chlorophyll (which is often used as a reflection of nitrogen status under field conditions—see, e.g., Fox R H et al 2001 Agron J. 93, 590-597; Minotti P L et al 1994 Hort Science 29, 1497-1550), amino acid levels, and nitrate reductase and glutamine synthetase activities in order to give a baseline in which to assess studies on mutant lines.

B. Expression Profiling Experiments on *Arabidopsis* Plants Under Nitrogen Limitation Transcript expression profiling can be used to test RNA levels of large numbers of genes at the same time. Large numbers of these types of experiments have been done in the past, and if the experimental system is amenable, these can be used to pinpoint the "expression status" of an organism under different conditions and to use this information to make hypotheses on what genes and pathways are involved in various processes. The inventors found that the more profound the difference in growth conditions, the larger the differences in transcript profiles between the plants grown under these conditions and the more difficult it was to decipher which changes were most important. The only published whole genome profiling experiment in this area is one in *Arabidopsis* where an extreme change in nitrate levels was studied (Wang R et al 2003 Plant Physiol. 132, 556-67). In the case of nitrogen limitations, the inventors studied the effect of growing plants under chronic nitrogen stress as well as changes in the level of available nitrogen. The inventors have already determined the impact on growth of different nitrogen levels in *Arabidopsis*.

The effect of different nitrogen levels on the transcript profiles was studied: where nitrogen does not limit growth. For *Arabidopsis* the inventors collected 4-week old shoots grown under the different nitrogen regimes. Three different samples were collected (biological triplicates) in order to get statistically significant results. The transcript profiling was done using *Arabidopsis* GeneChip® whole genome array (Affymetrix) to study the transcript levels in *Arabidopsis*. The bioinformatic analysis necessary to study the considerable data produced by these experiments was performed. By studying the effect of nitrogen limitation on the expression patterns, the inventors can pinpoint which pathways are involved in their response to nutrient stress Example 1

Cloning and Sequence of At5g56860

Gene predictions were derived from the sequence databases, and used to design oligonucleotide primers for PCR amplification of either full-length (inclusive of the predicted initiation and stop codons, for transgenic gene overexpression) or partial (for transgenic gene knockout) cDNA clones from rice first strand cDNA. In some instances, these PCR primers included additional 5' sequences for Gateway™ recombination-based cloning (Invitrogen). PCR amplification was carried out using the HF Advantage II (Clonetech) or EXPAND (Roche) PCR kits according to the manufacturer's instructions. PCR products were cloned into pCR2.1-TOPO or pDONR201 according to the manufacturer's instructions (Invitrogen).

DNAs from 4-8 independent clones were miniprepped following the manufacturer's instructions. DNA was subjected to sequencing analysis using the BigDye™ Terminator Kit according to manufacturer's instructions (ABI). Sequencing made use of primers designed to both strands of the predicted gene. All sequencing data were analyzed and assembled using the Phred/Phrap/Consed software package (University of Washington) to an error ratio equal to or less than 10-4 at the consensus sequence level.

Consensus sequences were validated as being intact and the correct gene in several ways. Initially, restriction analysis was used to confirm the presence of cDNA inserts of the expected sizes in individual clones. For full-length clones, the coding region was checked for absence of interruptions (predicted start and stop codons present, no internal stop codons), by sequencing of the cDNA insert. For both full-length and partial cDNA clones, alignment with the gene prediction and BLAST analysis was used to confirm that the intended target gene was amplified. All cDNA clones generated by PCR were cloned into custom-made binary destination vectors using Gateway™ recombination-based cloning per the manufacturer's instructions (Invitrogen) Alternatively, PCR products were cloned using conventional restriction enzyme-based cloning.

Expression Vectors and Transformation of Plants

Binary destination vectors for plant transformation consist of a binary backbone and a T-DNA portion. The binary backbone contains the sequences necessary for selection and growth in *Escherichia coli* DH-5α (Invitrogen) and *Agrobacterium tumefaciens* LBA4404, including the bacterial spectinomycin antibiotic resistance aadA gene from *E. coli* transposon Tn7, origins of replication for *E. coli* (ColE1) and *A. tumefaciens* (VS1), and the *A. tumefaciens* virG gene. The T-DNA portion was flanked by the right and left border sequences and includes the Positech™ (Syngenta) plant selectable marker and a gene expression cassette which varies depending on the application. The Positech™ plant selectable marker in this instance consists of a rice ACT1 (actin) promoter driving expression of the PMI (phosphomannose isomerase) gene, followed by the cauliflower mosaic virus transcriptional terminator, and confers resistance to mannose.

The gene expression cassette portion of the binary destination vectors varies depending on the application. In general, the cassette consists of a promoter designed to express the gene in certain tissues of the plant, followed by cloning sites (in some cases interrupted by a segment of spacer DNA), and finally by the *A. tumefaciens* nos 3' end transcriptional terminator. The promoters used are designed to express the gene of interest in specific target tissues (eg. endosperm: rice RS-4, wheat glutelin, maize ADPgpp or γ-zein, or barley α-thionin; eg. embryo: maize globulin or oleosin; eg. aleurone: barley α-amylase; eg. root: maize MSR1 and MRS3; eg. green tissue: maize PEPC) or constitutively (eg. maize UBI plus intron), depending on the gene of interest. The cloning site contains either unique restriction enzyme sites (for conventional cloning) and/or a Gateway™ recombination-based cloning cassette (Invitrogen), in either the forward or reverse orientation. In gene expression cassettes designed for double-stranded interfering RNA (dsRNA) production, the cloning site is divided by a spacer region (eg. first intron of the rice SH1 gene). The spacer, permits the cloning of two gene fragments one in the forward and one in the reverse orientation. Antisense (reverse orientation expression) is another technology available for silencing genes of interest.

Transformation of the nucleic acid molecules of the present invention into plants was performed using methods described above in the Detailed Description. Test kits for detection of plants containing the nucleic acid molecules of the present invention can be produced using general techniques for the production of antibodies for the use in ELISA-type immunoassays. Alternatively, kits for PCR-type analysis of plant DNA can be used to test for the presence of the nucleic acid molecules of the present invention.

Results

Loss of the At5g56860 Gene Expression Causes Reduced Chlorophyll Level in the T-DNA Insertion Line Plants homozygous for the T-DNA insertion mutation in the At5g56860 gene were identified and screened for any phenotypic change. The leaves of the mutant plants were pale green due to a reduced total chlorophyll level. The At5g56860 gene exhibited a single zinc finger with 18 residues in the zinc finger loop (C-X2-C-X18-C-X2-C). The full length protein sequence contains 398 amino acids. The T-DNA insertion (SALK_001778) was close to the end of the second exon, causing deletion of the GATA domain. The expression of the At5g56860 was not detected in the mutant by RT-PCR.

To determine if the phenotype change of the SALK_001778 line was caused by the single gene mutation, the inventors made the construct to over-express the Atg56860 gene and transformed this gene back into the mutant line. The phenotype in the mutant was complemented in the transformants in which the expression of the At5g56860 gene was detected, demonstrating that the At5g56860 gene was responsible for the reduced chlorophyll phenotype change in the SALK_001778 mutant line.

The mutant was also back-crossed to wild type and heterozygous plants were identified by PCR having both the wild type and the insertion allele. These plants were allowed to self propagate and the progeny seeds showed a 3:1 segregation with the mutant phenotype being present only in those plants homozygous for the T-DNA insertion in the At5g56860 gene, indicating that the mutant phenotype was caused by the single At5g56860 gene mutation and that this was recessive to the wild-type allele.

The expression of the At5g56860 Gene is Tissue-Specific and is Regulated by the Nitrate Status; Same Trend as the Nitrate Assimilation Genes In order to determine the expression pattern of the AtSg56860 gene, total RNA from buds, leaves and roots was extracted and cDNA made. RT-PCR was used to determine the expression pattern of this gene and demonstrated that the At5g56860 gene was expressed in buds and leaves but not in roots. To determine the expression of this gene during development, seedlings germinated on MS medium after 3 days and 5 days were harvested and total RNA extracted. The At5g56860 gene was found to be expressed right after germination.

Since chlorophyll level is often used as a reflection of nitrogen status (29-30—need references), the expression of the gene was studied under different nitrogen conditions to determine if its expression level is influenced by nitrogen availability. The baseline expression level of the At5g56860 grne was lower when grown in a hydroponic culture with very low nitrate concentration (0.3 mM) comparing with high concentration (3 mM). In order to determine whether this gene is regulated by nitrate, the plants were transferred from 1 mM nitrate to the 3 mM nitrate growth conditions. The expression of the At5g56860 gene was up-regulated by the increased nitrate concentration after 2 hrs, with the level of expression level decreasing after 24 hr although it was still above the baseline expression level. The same expression pattern was found for the nia1, nia2, and nir, the first two enzymes in nitrate reduction, although the magnitude of fold change was larger for nia1, nia2 and nir than for the At5g56860 gene.

The At5g56860-Less Plant Accumulates Less Total N when N Supply is Limiting but the At5g56860 Seems not to Directly Regulate the Expression of Nitrate Assimilation Genes Since At5g56860 expression is influenced by the nitrogen status, the inventors tested if different nitrogen conditions would affect the growth of the mutant plant. The mutant and wild type plants were grown on conditions limiting for N when the plants are grown in soil (3 mM nitrate) and the ideal nitrogen condition (10 mM nitrate). Shoots of the 4-week-old mutant and the control plants were collected, with biomass and total N being measured. There was no significant change in biomass. However, the total N in the mutant was less than in wild type under limiting N condition and similar to wild type plants when there was sufficient N supply. The expression of nia1, nia2, and nir was analyzed in the mutant plants using real time PCR which showed that nia1, nia2 and nir expression in the mutant was not significantly different from that in the wild type plant. If the At5g56860 gene is one of the regulatory genes directly controlling nia1, nia2 and nir expression, the baseline expression level of nia1, nia2 and nir would be altered in the T-DNA mutant lacking the At5g56860 expression. However, this was not the case.

The At5g56860 Gene Regulates the Expression of Genes Involved in Different Functional Categories A transcriptional profiling experiment was done to compare the baseline gene expression at a whole genome scale in the mutant and the wild type plant to see which genes have altered expression in the mutant. Again, wild type plants and the SALK_001778 mutant plants were grown under either limiting N condition (3 mM nitrate) or sufficient N condition (10 mM nitrate) and 4-week-old shoots were collected. RNA were extracted and hybridized to *Arabidopsis* GeneChip® whole genome array. Genes having at least 1.5 times lower expression in mutant versus wild-type plants grown under limiting N condition (3 mM nitrate) and genes having at least 1.5 times lower expression in mutant versus wild-type plants when grown at sufficient N concentration (10 mM) were analyzed. A browser-based functional classification program (Provart, N. & Zhu, T. (2003) Currents in Computational Molecular Biology 271-272) was used to show that the down-regulated genes include those involved in nitrogen and sulfur metabolism (At3g44300 and At4g27450), in the regulation of C-compounds and carbohydrate utilization (At2g18700 and At1g70290), in the biosynthesis of lipid, secondary metabolism, glycosides (At4g37150, At1g09500, At3g09260), in perception of nutrients and nutritional adaptation (At5g24160), in nutrients uptake and absorption (At1g03220 and At2g37770), in electron transport and membrane-associated energy conservation (At5g24160 and At5g20230). The inventors verified some of those genes by quantitative RT-PCR and the correlation between the PCR and microarray data was very high.

The At5g56860 Mutant Plant is More Sensitive to Exogenous Glucose

While the At5g56860 appears to regulate the expression of genes important for different biological processes, many of these genes are involved in C metabolism, such as the sugar and hexose transporters. In order to test whether the growth of the mutant plant would be different from the wild type on different C source, these plants were germinated on different concentration of glucose and sucrose. The average growth of the mutant seedlings were stunted compared with the wild type plants on a 6% glucose medium Seedling phenotypes on plates containing 6% glucose are well-documented bioassays for sugar sensitivity (Jang, J., Leon, P, Zhou, L. & Sheen, J.

(1997) Plant Cell 9, 5-19) and the results showed that the mutant with no expression of the At5g56860 is hypersensitive to 6% glucose.

The At5g56860 Gene Appears to Regulate the Expression of HXK1 but not HKX2 and Also Regulates the Hexose Transporter Gene The At5g56860 gene affects sensitivity to glucose and thus would be expected to affect the expression of genes involved in glucose metabolism. Two types of genes have been shown to affect glucose sensing. The first is hexokinase (HXK) since over-expression of HXK in this gene leads to a phenotype quite similar to that of the insertion mutation in the At5g56860 GATA transcription factor gene. The second is the hexose transporter gene which has been shown to be involved in sugar sensing in yeast. There are two *Arabidopsis* HXK genes which were identified by genetic complementation of a yeast hxk1hxk2 double mutant (Jang, J., Leon, P, Zhou, L. & Sheen, J. (1997) Plant Cell 9, 5-19). The results showed that the baseline HXK1 expression level was higher in the mutant comparing to that in the wild type, but the HXK2 level was not altered at all in the mutant, suggesting that the At5g56860 is a negative regulator of HXK1 but not HXK2.

The 500 bp upstream sequence of HXK1 and HXK2 were searched and the consensus GATA binding sequence (T/A)GATA(G/A), or (T/C)TATC(T/A) on the complementary strain, was present multiple times in the HXK1 promoter sequence, while it was absent from the HXK2 promoter sequence (sequence not shown). The hexose transporter gene was down-regulated in the mutant line and also had the GATA motif present in its promoter region. Although, the presence of a GATA motif is not definitive in demonstrating the regulation of HXK1 and the hexose transporter by a GATA factor, their presence at least supports the notion that it might be directly regulating these genes.

Gain-of-Function Transgenic Plants are Sugar Hyposensitive

Transgenic *Arabidopsis* plants overexpressing the At5g56860 were generated by *Agrobacterium*-mediated transformation (Bechtold, N., Ellis, J. & Pelletier, G. (1993) C R Acad Sci 316, 1194-1199). Transgenic plants were selected on kanamycin containing medium and T2 lines showed a 3:1 segregation ratio on kanamycin which indicate a single insertion of the transgene. These were selected for self pollination. Transgenic lines of the T3 generation homozygous for the transgene were used for further analysis. The expression levels of At5g56860 in the transgenic lines were determined by real-time RT-PCR (data not shown). The seeds from over-expressing lines were germinated on 6% glucose plates and there was little inhibitory affect on growth for the over-expressing transgenic seedlings, while wild-type plants are severely inhibited, indicating they are much less sensitive to the exogenous glucose. It is interesting to note that the HXK1 gene is not down regulated in these transgenic lines (data not shown) while the hexose transporter gene is strongly up-regulated in these plants.

Discussion

The At5g56860 is Required for the Sugar Sensing

In the T-DNA mutant with no expression of the At5g56860 gene, the mutants were sugar hypersensitive, while the transgenic plants over-expressing the At5g56860 gene show sugar hyposensitivity, demonstrating that the At5g56860 is involved in the regulation of sugar sensing. The hypersensitivity to 6% glucose has been reported in transgenic *Arabidopsis* plants overexpressing AtHXK1 and AtHXK2 (Jang, J., Leon, P, Zhou, L. & Sheen, J. (1997) Plant Cell 9, 5-19) and the hyposensitivity to 6% glucose was reported in the transgenic *Arabidopsis* plants expressing antisense AtHXK1 and AtHXK2 (Jang, J., Leon, P, Zhou, L. & Sheen, J. (1997) Plant Cell 9, 5-19). Transgenic seedlings overexpressing AtHXK1 were reported to have reduced chlorophyll content in their leaves (Jang, J., Leon, P. Zhou, L. & Sheen, J. (1997) Plant Cell 9, 5-19; Dai, N., Schaffer, A., Petreikov, M., Shahak, Y., Giller, Y., Ratner, K., Levine, A. & Granot, D. (1999) Plant Cell 11, 1253-1266). In the T-DNA mutant with no expression of the At5g56860, the AtHXK1 baseline line expression is higher than the wild type control and they are sugar hypersensitive. The mutants show a reduced chlorophyll level. No GATA elements are found in the 500 bp upstream sequence of the HXK2 structural gene. There is one GATA element in the −737 region of the HXIQK promoter. However, since tandem repeat or two GATA elements located within 30 bp or the core sequence (T/A)GATA(G/A) is required for efficient binding (Chiang, T. Y. & Marzluf, G. A. (1994) Biochemistry 33, 576-582; Lin, Y., Hwang, C. F., Brown, J. B. & Cheng, C. L. (1994) Plant Physiol 106, 477-484), it is unlikely that HXK2 is directly regulated by GATA factors. On the contrary, the 500 bp upstream sequence of the HXK1 has a number of GATA elements. The level of HXK1 expression is altered in the At5g56860 mutant line, but not the HXK2 which supports the notion that this GATA factor regulates the expression of HXK1.

The lines over-expressing At5g56860 are resistant to the presence of high glucose levels. The over-expression of this GATA factor does not lead to a change in expression of HXK1, but does lead to an increase in expression of the hexose transporter gene. This gene has been found to be involved in sugar sensing in yeast.

The At5g56860 Expression Responds to a Change of the N Status

The At5g56860 gene expression is apparently influenced by the N status of the plant. When the nitrate level is low, the baseline expression of the At5g56860 gene is relatively low and when the nitrate level is high, the baseline expression level of the At5g56860 gene is relatively high. When plants are switched from low nitrate condition to higher nitrate condition, the expression of the At5g56860 gene is up-regulated. This expression pattern is the same as the key enzymes in the nitrate assimilation pathways such as NR and NiR, although the latter have higher rates of induction of expression when exposed to high levels of nitrate. However, the At5g56860 gene does not directly control nia1, nia2 and nir expression as these are not affected in the mutant line. The expression of the At5g56860 gene does have an impact on nitrogen metabolism, as loss of the At5g56860 gene resulted in reduced total N accumulation. It is interesting to note that the At5g56860 gene forms a paralogous relationship with the At4g26150 gene from the phylogenetic tree of all 30 *Arabidopsis* GATA transcription factor genes (Riechmann, J. L., Heard, J., Martin, G., Reuber, L., Jiang, C., Keddie, J., Adam, L., Pineda, O., Ratcliffe, O. J., Samaha, R. R., Creelman, R., Pilgrim, M., Broun, P., Zhang, J. Z., Ghandehari, D., Sherman, B. K. & Yu, G. (2000) Science 290, 2105-2110; Reyes, J. C., Muro-Pastor, M. I. & Florencio, F. J. (2004) Plant physiol. 134, 1718-1732). The At4g26150 has already been shown to be inducible by nitrate (Wang, R., Okamoto, M., Xing, X. & Crawford, N. M. (2003) Plant Physiol 132, 556-567; Scheible, W., Morcuende, R., Czechowski, T., Fritz, C., Osuna, D., Palacios-Rojas, D., Schindelasch, D., Thimm, O., Udvardi, M. K. & Stitt, M. (2004) Plant Physiol 136, 2483-2499). However, their function does not seem to be redundant as the expression signatures are not completely the same for the two genes (Czechowski, T., Bari, R., Stitt, M., Scheible, W. & Udvardi, M. (2004) Plant J. 38, 366-379). In the SALK_001778 mutant where At5g56860 gene expression is lost, the expression of the At4g26150 gene is increased but this did not complement the mutant phenotype.

Crosstalk Between the C and N Regulation

It is a challenge to understand how the C and N signaling pathways interact with each other, not to mention their interaction with other signaling pathways such as those involved with hormones, light and stress. To the knowledge of the present inventors, this is the first trans-acting factor reported to be involved in regulating sugar sensing and it is important to note that the expression of the factor itself is influenced by the change of the N status.

Example 2

The full length At5g56860 cDNA (GNC) was amplified from Arabidopsis leaf cDNA using the primers 5'-GCTCTA-GATTTCTCTCTCTCTTTGTGTCTTCATTTG-3' (SEQ ID NO:4) and 5'-gcgagctctcgggtgactaatgttcgttcc-3' (SEQ ID NO:5). The resulting ~1500 bp fragment was verified by sequencing and then digested by XbaI and SacI and cloned into the XbaI-SacI-digested expression vector pROK2 containing the cauliflower mosaic virus (CaMV) 35S promoter driving the GNC expression in a constitutive, high-level fashion (FIG. 4). The p35S-GNC binary vector was transformed into Agrobacterium tumefaciens strain EHA105 and the resulting Agrobacterium strain was used to transform the wild type plants (Col-0) and the transformants were selected on kanamycin resistance. Plants with a single insertion of the transgene were selected for self pollination to generate T3 homozygous lines for further analysis. Over-expression of GNC in the transgenics was confirmed by quantitative RT-PCR. Wild type plants and GNC over-expression plants were grown under sufficient nitrogen (10 mM nitrate) and limiting nitrogen (3 mM nitrate) conditions. No obvious difference was observed in the initial growth stages for both nitrogen conditions. After ~28 days when plants started entering the reproductive stage, leaf senescence was observed in the wild type plants grown under limiting nitrogen condition but not in the GNC over-expression plants and this difference in senescence was clearly observable in the period after this stage. In addition, total chlorophyll level was ~15% higher in those GNC over-expression plants. The chlorophyll level is an indicator of nitrogen availability and photosynthetic capacity indicating that these over-expressing lines are healthier under a reduced nitrogen regime. Neither wild type nor GNC over-expression plants of 4-week-old showed these differences under the sufficient nitrogen condition. There was no significant difference in chlorophyll level between wild type and GNC over-expression plants under sufficient nitrogen condition.

Having now described particular embodiments of the invention by way of the foregoing examples, which are not intended to be limiting, the invention will now be further set forth in the following claims. Those skilled in the art will recognize that the claims also permit for the inclusion of equivalents beyond the claims' literal scope.

What is claimed is:

1. A method of producing a transgenic plant comprising:
   (a) transforming a plant cell with a nucleic acid molecule comprising SEQ ID NO:3; and
   (b) growing the plant cell into a plant that expresses SEQ ID NO:3 wherein expressing the nucleic acid molecule results in an elevated level of expression of SEQ ID NO:3 as compared to a plant that has not been transformed with SEQ ID NO:3; and
   (c) selecting a transgenic plant having improved or increased nitrogen utilization, carbon utilization, seed yield, or chlorophyll levels.

2. The method according to claim 1, wherein the plant is a dicot, gymnosperm, or a monocot.

3. The method according to claim 2, wherein the monocot is selected from the group consisting of maize, wheat, barley, oats, rye, millet, sorghum, triticale, secale, einkorn, spelt, emmer, teff, milo, flax, gramma grass, *Tripsacum* sp., and teosinte.

4. The method according to claim 2, wherein the dicot is selected from the group consisting of soybean, tobacco, or cotton.

5. The method according to claim 1, wherein the nucleic acid molecule is expressed in a specific location or tissue of the plant.

6. The method according to claim 5, wherein the location or tissue is selected from one or more of seed, epidermis, root, vascular tissue, meristem, cambium, cortex, pith, leaf, and flower.

7. The method according to claim 6, wherein the location or tissue is a seed.

8. The method according to claim 1, wherein the nucleic acid molecule is in an expression cassette comprising a promoter sequence operably linked to the nucleic acid molecule.

9. A method of producing a transgenic plant comprising:
   (a) transforming a plant cell with a nucleic acid molecule comprising a nucleic acid sequence shown in SEQ ID NO: 3 or a sequence that hybridizes to SEQ ID NO: 3 under stringent hybridization conditions comprising 7% sodium dodecyl sulfate (SDS), 0.5 M $NaPO_4$, 1 mM EDTA at 50° C. with washing in 0.2×SSC at 65° C., wherein the sequence that hybridizes encodes a functional GATA transcription factor;
   (b) growing the plant cell into a plant that expresses SEQ ID NO:3 wherein expressing the nucleic acid molecule results in an elevated level of expression of SEQ ID NO:3 as compared to a plant that has not been transformed with SEQ ID NO:3; and
   (c) selecting a transgenic plant having improved or increased nitrogen utilization, carbon utilization, seed yield, or chlorophyll levels.

10. The method according to claim 9, wherein the plant is a dicot, gymnosperm, or a monocot.

11. The method according to claim 10, wherein the monocot is selected from the group consisting of maize, wheat, barley, oats, rye, millet, sorghum, triticale, secale, einkorn, spelt, emmer, teff, milo, flax, gramma grass, *Tripsacum* sp., and teosinte.

12. The method according to claim 10, wherein the dicot is selected from the group consisting of soybean, tobacco, or cotton.

13. The method according to claim 9, wherein the nucleic acid molecule is expressed in a specific location or tissue of the plant.

14. The method according to claim 13, wherein the location or tissue is selected from one or more of seed, epidermis, root, vascular tissue, meristem, cambium, cortex, pith, leaf, and flower.

15. The method according to claim 14, wherein the location or tissue is a seed.

16. The method according to claim 9, wherein the nucleic acid molecule is in an expression cassette comprising a promoter sequence operably linked to the nucleic acid molecule.

* * * * *

UNITED STATES PATENT AND TRADEMARK OFFICE
CERTIFICATE OF CORRECTION

PATENT NO. : 8,586,825 B2  Page 1 of 1
APPLICATION NO. : 12/494171
DATED : November 19, 2013
INVENTOR(S) : Rothstein et al.

It is certified that error appears in the above-identified patent and that said Letters Patent is hereby corrected as shown below:

On Title Page:
Item 56, References Cited, page 1, right column:
    Please delete the text at the end of the section reading "(Continued)"

In the Specification:
Column 4, Line 8: Please correct "Howift S M and Udvardi"
    to read -- Howitt S M and Udvardi --

Column 4, Line 40: Please correct "(Roland, F., Moore,"
    to read -- (Rolland, F., Moore, --

Column 4, Lines 65-66: Please correct "Stift, M., Müller, M., Maft, M.,"
    to read -- Stitt, M., Müller, M., Matt, M., --

Column 45, Line 32: Please correct "at least 99% identical"
    to read -- at least 99% identical. --

Column 54, Line 49: Please correct "Publishers (1.998)."
    to read -- Publishers (1998). --

In the Claims:
Column 68, Claim 9, Line 4: Please correct "washing in 0.2×SSC at"
    to read -- washing in 0.2X SSC at --

Signed and Sealed this
Thirtieth Day of September, 2014

Michelle K. Lee
*Deputy Director of the United States Patent and Trademark Office*

```
                        SEQUENCE LISTING

<160> NUMBER OF SEQ ID NOS: 5

<210> SEQ ID NO 1
<211> LENGTH: 1197
<212> TYPE: DNA
<213> ORGANISM: Arabidopsis thaliana

<400> SEQUENCE: 1
atggattcaa attttcatta ctcgatagat cttaacgaag atcaaaacca tcacgaacaa      60 cccttttct atcctcttgg atcctcttcc tcgcttcatc atcatcatca tcatcatcat     120
catcaagtcc cttctaattc ttcatcttct tcttcgtcca tttcatcgct ctcctcttac     180
ctccctttct tgatcaactc tcaagaagat caacatgttg cctacaacaa cacttatcac     240
gctgatcatc tccatctttc tcaaccctc aaggccaaga tgtttgtggc taacggtgga     300
tcatcagcat gcgatcacat ggtgccaaag aaggagacaa gactgaaact aacgataagg     360 aaaaagatc acgaagacca accccatcct cttcatcaaa acccgacaaa acccgattca     420
gactccgaca agtggttgat gtcccaaag atgcggttga tcaagaaaac aatcaccaac     480
aataaacagc tcattgatca gactaataat aataatcata agaaagtga tcactaccct     540 ttgaatcata agactaattt cgacgaggat caccatgaag atcttaattt caagaacgtc     600
ttgaccagga agaccacggc cgcgaccacc gagaatcgct acaatacaat caacgagaac     660
ggttatagta ataacaatgg cgtgattagg gtttgttcgg attgtaacac caccaagact     720
cctctttggc gaagtggacc tcgaggtccc aagtctcttt gtaacgcatg tggtatacgg     780
caaagaaagg caaggcgagc cgctatggcc gcggccgctg cagccggcga ccaagaggtg     840
gcggtagcgc cccgagtgca acaattaccg ctgaaaaaga agttgcaaaa taaaaaaaag     900
agatcaaacg gaggggaaaa atacaatcac tctcctccaa tggtggccaa ggccaaaaag     960
```

-continued

```
tgcaagatca aagaggaaga ggagaaggaa atggaagcgg aaacggttgc cggagattca   1020
gagatcagca atctacaac ttcttctaat tcttcgattt cgtcaaacaa attttgcttc    1080
gatgatttga caataatgtt gagcaaaagc tcagcttatc aacaagtgtt cccacaagat   1140
gagaaggagg ctgctgtttt gctcatggct ctgtcgtatg aatggttca cggttga       1197
```

```
<210> SEQ ID NO 2
<211> LENGTH: 398
<212> TYPE: PRT
<213> ORGANISM: Arabidopsis thaliana

<400> SEQUENCE: 2

Met Asp Ser Asn Phe His Tyr Ser Ile Asp Leu Asn Glu Asp Gln Asn
1               5                   10                  15

His His Glu Gln Pro Phe Phe Tyr Pro Leu Gly Ser Ser Ser Ser Leu
            20                  25                  30

His His His His His His His His Gln Val Pro Ser Asn Ser Ser
        35                  40                  45

Ser Ser Ser Ser Ser Ile Ser Ser Leu Ser Ser Tyr Leu Pro Phe Leu
    50                  55                  60

Ile Asn Ser Gln Glu Asp Gln His Val Ala Tyr Asn Asn Thr Tyr His
65                  70                  75                  80

Ala Asp His Leu His Leu Ser Gln Pro Leu Lys Ala Lys Met Phe Val
                85                  90                  95

Ala Asn Gly Gly Ser Ser Ala Cys Asp His Met Val Pro Lys Lys Glu
            100                 105                 110

Thr Arg Leu Lys Leu Thr Ile Arg Lys Lys Asp His Glu Asp Gln Pro
        115                 120                 125

His Pro Leu His Gln Asn Pro Thr Lys Pro Asp Ser Asp Ser Asp Lys
    130                 135                 140

Trp Leu Met Ser Pro Lys Met Arg Leu Ile Lys Lys Thr Ile Thr Asn
145                 150                 155                 160

Asn Lys Gln Leu Ile Asp Gln Thr Asn Asn Asn His Lys Glu Ser
                165                 170                 175

Asp His Tyr Pro Leu Asn His Lys Thr Asn Phe Asp Glu Asp His His
            180                 185                 190

Glu Asp Leu Asn Phe Lys Asn Val Leu Thr Arg Lys Thr Thr Ala Ala
        195                 200                 205

Thr Thr Glu Asn Arg Tyr Asn Thr Ile Asn Glu Asn Gly Tyr Ser Asn
    210                 215                 220

Asn Asn Gly Val Ile Arg Val Cys Ser Asp Cys Asn Thr Thr Lys Thr
225                 230                 235                 240

Pro Leu Trp Arg Ser Gly Pro Arg Gly Pro Lys Ser Leu Cys Asn Ala
                245                 250                 255

Cys Gly Ile Arg Gln Arg Lys Ala Arg Arg Ala Ala Met Ala Ala Ala
            260                 265                 270

Ala Ala Ala Gly Asp Gln Glu Val Ala Val Ala Pro Arg Val Gln Gln
        275                 280                 285

Leu Pro Leu Lys Lys Leu Gln Asn Lys Lys Arg Ser Asn Gly
    290                 295                 300

Gly Glu Lys Tyr Asn His Ser Pro Pro Met Val Ala Lys Ala Lys Lys
305                 310                 315                 320

Cys Lys Ile Lys Glu Glu Glu Lys Glu Met Glu Ala Glu Thr Val
                325                 330                 335

Ala Gly Asp Ser Glu Ile Ser Lys Ser Thr Thr Ser Ser Asn Ser Ser
```

```
                340               345              350
Ile Ser Ser Asn Lys Phe Cys Phe Asp Asp Leu Thr Ile Met Leu Ser
            355                  360                  365

Lys Ser Ser Ala Tyr Gln Gln Val Phe Pro Gln Asp Glu Lys Glu Ala
    370                  375                  380

Ala Val Leu Leu Met Ala Leu Ser Tyr Gly Met Val His Gly
385                 390                 395

<210> SEQ ID NO 3
<211> LENGTH: 1044
<212> TYPE: DNA
<213> ORGANISM: Oryza sativa

<400> SEQUENCE: 3
atgtctacca tctacatgag tcagctctca gctgctctcc ctctcatgga gggggagcac     60
caccatcacc accaggatca tcaccaaggc cacttccaag ccttctccct gcagcctaag    120 gatccccag tcttattccc ctttgtgatc agtagaagaa gcagcagcag cagccctagc    180
gacagcacca ctctaagcta tggttcagac catcacttga cacagcagca gcagcatcag    240
catcaagcca tgcttgagcc ccaaaatatg attggaggat catccgctgg catctttgcg    300
acgccgttcc cgaccgtcaa gagcatccgc gacgacatga tcgagcggtc gcagttcgat    360
ccatacgata ccgagaagct gcaggcgagc tgcgggttag ccaaggtcgt cgccggcggc    420
aagtggagcg cggtgccagc ggccaagatg aagatcacga ggaagatggg tgagccgtcg    480
tccggtgtca ctggcggggc tgcgacgacg gtggcgccga agaagccgag gaggaggccg    540
gcgcaggcgt acgaggatca cggccatggc ggcgccatgg gccaagcttt tggcgtgatt    600
agggtgtgct ccgactgcaa caccaccaag actcccttgt ggaggagtgg cccgtgcggc    660
cccaagtcgc tttgcaacgc gtgcggcatc aggcagagga aggcgcggcg ggcgatgatg    720
gcctccggac taccagcgtc ccccaacgcc gccggcccca aggcggccgc acatagcggc    780
gccacaaacg cagccgccgc agctgccatg gaggagacgg ccgagtccgc caccgtcgcc    840
ccgcccccgg cgccgacgac gaggggtggt actctcgtcg acagcatcgg gctcagctgg    900
agcaagaccc atgccgccgc caccgcctcc tgcagcttcc ggccgtcacc ggtggctccc    960
ggcttcgcgg cggcggtgca ggacgagatc actgacgccg ccatgctgct catgacgctg   1020
tcctgcgggc ttgtccggag ctga                                          1044

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
gctctagatt tctctctctc tttgtgtctt catttg                                36

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
gcgagctctc gggtgactaa tgttcgttcc                                       30
```